(12) United States Patent
Yasue et al.

(10) Patent No.: US 6,569,618 B1
(45) Date of Patent: May 27, 2003

(54) DIAGNOSIS OF DISEASES ASSOCIATED WITH CORONARY TWITCHING

(75) Inventors: Hirofumi Yasue, Kumamoto (JP); Michihiro Yoshimura, Kumamoto (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/068,506

(22) PCT Filed: Nov. 13, 1996

(86) PCT No.: PCT/JP96/03324

§ 371 (c)(1),
(2), (4) Date: Jul. 10, 1998

(87) PCT Pub. No.: WO97/18327

PCT Pub. Date: May 22, 1997

(30) Foreign Application Priority Data

Nov. 13, 1995 (JP) .............................................. 7-319504
Jun. 28, 1996 (JP) .............................................. 8-168761

(51) Int. Cl.[7] .............................. C12Q 1/68; C12P 19/34
(52) U.S. Cl. ......................................... 435/6; 435/91.1
(58) Field of Search ................... 435/6, 91.2; 536/22.1, 536/23.1

(56) References Cited

PUBLICATIONS

Marsden et al J. Biol. Chem 268:17478–17488, 1993.*
Nadaud et al. Biochem.Biophy.Res.Comm 198:1027–1033, 1994.*
Janssens, Stefan P. et al., *The Journal of Biological Chemistry*, vol. 267, No. 21, Jul. 25, 1992, pp. 14519–14522.
Marsden, Philip A. et al., *FEBS Letters*, vol. 307, No. 3, Aug. 1992, pp. 287–293.
Nadaud, Sophie et al., *Biochemical and Biophysical Research Communications*, vol. 198, No. 3, Feb. 15, 1994, pp. 1027–1033.
Marsden, Philip A. et al., *The Journal of Biological Chemistry*, vol. 268, No. 23, Aug. 15, 1993, pp. 17478–17488.
Miyahara, Kaoru et al., *Eur. J. Biolchem.*, vol. 223, 1994, pp. 719–726.

* cited by examiner

*Primary Examiner*—Eggerton A. Campbell
(74) *Attorney, Agent, or Firm*—Birch, Stewart, Kolasch & Birch, LLP

(57) ABSTRACT

The present invention relates to a process for screening for a gene involving a coronary artery spasm-associated disease, which comprises detecting the presence of the relevant nucleotide substituents in the endothelial nitric oxide synthase (eNOS) gene. The present invention provides the ready diagnosis of a coronary artery spasm-associated disease such as angina, which cannot be conveniently screened by the conventional methods.

13 Claims, 5 Drawing Sheets

FIG. 1

DIAGNOSIS OF DISEASES ASSOCIATED WITH CORONARY TWITCHING

This application claims the benefit under 35 U.S.C. §371 of prior PCT International Application No. PCT/JP96/03324, which has an International filing date of Nov. 13, 1996, which designated the United States of America, the entire contents of which are hereby incorporated by references.

TECHNICAL FIELD

The invention relates to a technique for a diagnosis of a specific disease, and in particular, to a process for screening for a gene involving a coronary artery spasm-associated disease.

BACKGROUND ART

Intrinsic nitric oxide (intrinsic NO) is a substance which recently has been identified in vivo, and has been shown to act as a vasodilator (18–25), a neurotransmitter (11, 12) or an immunoreactant (13–17). The intrinsic NO is synthesized from L-arginine due to a family consisting of at least three nitric oxide synthases (NOSs), i.e., neural NOS, endothelial NOS, and macrophage NOS. Neural NOS and endothelial NOS are constitutive, and enhanced in their activity depending on concentrations of intracellular calcium. On the other hand, macrophage NOS is independent of calcium, and activated by inflammation. Early, some researchers determined the gene structure of endothelial cell nitric oxide synthase (eNOS), and reported that the eNOS gene locates at 7q35-36 in chromosome, and is composed of 26 exons, and spans 21 kb (18–25).

DISCLOSURE OF INVENTION

Coronary artery spasm is understood to be a pathogenic factor of various ischemic heart diseases such as coronary spastic angina and variant angina (1–6). However, a mechanism of the coronary spasm is not known well.

Thus, the present inventors have carried out investigations for clarifying the mechanism of the coronary spasm, considering that such investigations may contribute to development of an early diagnosis and treatment of the ischemic diseases to be associated with the coronary spasm. It should be noted that most of the previous studies have pointed out that a hyper-contractility of smooth muscle is more important in the pathogenic mechanism of the coronary spasm rather than a damage of hemangioendothelium (35).

Acetylcholine generally acts on smooth muscle to contract it, but acetylcholine eventually may lead vasodilatation by means of secretion of nitric oxide (NO) acting on smooth muscle, when the endothelium is uninjured. However, coronary administration of acetylcholine into patients having coronary spastic angina induces the coronary spasm rather than vasodilatation (7,8). In connection with this fact, the present inventors previously have demonstrated that the basal secretion of NO caused by acetylcholine is low in the patients having coronary spastic angina (10).

Since nitroglycerin and a nitrous acid medicine can effect vasodilatation in the course of forming NO in vivo the basal secretion of NO might be decreased in the coronary artery of the patients having coronary spastic angina, which is supported by the fact that the reaction of vessel in which the NO synthesis is suppressed, to the nitrous acid medicine is supersensitive (9), and the coronary artery in the patients having coronary spastic angina is supersensitive to nitroglycerin. These results would suggest the possibility of a strong relationship between coronary spasm and NO, specifically the endothelium where NO is secreted. To date, no one has paid attention to the relationship between coronary spasm and the endothelium where NO is secreted, except under the circumstance that the decrease in basal secretion of NO is known.

From a different point of view, the present inventors have noticed that coronary spasm may be caused by a genetic background in the light of the fact that coronary spasm is more frequent in Japan than in United States of America and Europe (26, 27).

On the basis of the above findings, the present inventors have focused on a gene of one of NOS enzymes which produce intrinsic NO, i.e., endothelial cell nitric oxide synthase (eNOS), examined if the gene is responsible for a development of coronary spasm, and finally completed the present invention.

SUMMARY OF THE INVENTION

The present invention relates to a process for screening for a gene involving a coronary artery spasm-associated disease, which comprises (obtaining DNA sample from a subject tested for a coronary artery spasm-associated disease, and) detecting the presence of one or more nucleotide changes in the gene of endothelial nitric oxide synthase (eNOS), which changes are selected from a group consisting of the changes from guanine (G) to thymine (T) at position 894 and from cytosine (C) to thymine (T) at position 774 of the cDNA sequence of the eNOS gene (of SEQ ID NO:2), and the changes from thymine (T) to cytosine (C) at position −786, from adenine (A) to guanine (G) at position −922 and from thymine (T) to adenine (A) at position −1468 of the 5'-flanking region of the eNOS gene, as well as the changes at the corresponding positions in the complementary strand thereof. Preferably, the present invention relates to the above process which comprises detecting the presence of two or more nucleotide changes selected from any one of nucleotide changes in the eNOS gene, and any one of nucleotide changes in the 5'-flanking region thereof, and more preferably, to the above process in which the coronary artery spasm-associated disease is angina, and further preferably, to the above process in which the coronary artery spasm-associated disease is coronary spastic angina.

In one aspect, the present invention relates to the process for screening for the above changes which comprises RFLP method wherein the presence or absence of a cleavage caused by a restriction enzyme is detected. Particularly, the present invention relates to the process in which the detection of the presence of the changes is performed by amplifying the relevant region to exon 7 in the cDNA coding eNOS by means of PCR, digesting the amplified fragments with the restriction enzyme(s) BanII and/or MboI, and electrophoresing the fragments digested with the enzyme, as well as the process in which the detection of the presence of the changes in exon 6 is performed by treating with the restriction enzyme FokI, the process in which the detection of the presence of the changes at position −786 in the 5'-flanking region of the eNOS gene by treating with the restriction enzyme MspI, and the process in which the detection of the presence of the changes at position −1468 in the 5'-flanking region of the eNOS gene by treating with the restriction enzyme MboI.

In one aspect, the present invention relates to a kit for performing the process of the present invention, and specifically, to a kit for diagnosing a coronary artery spasm-associated disease, which comprises (a pair of) amplification (oligonucleotides) for amplifying the relevant portion to exon 7 in the cDNA coding eNOS by PCR, and the restriction enzyme(s) BanII and/or MboI; a kit for diagnosing a coronary artery spasm-associated disease, which comprises an amplification oligonucleotide for amplifying the relevant portion to exon 6 in the cDNA coding eNOS by PCR, and the restriction enzyme FokI; a kit for diagnosing a coronary artery spasm-associated disease, which comprises an amplification oligonucleotide for amplifying a portion encompassing the −786 position in the 5'-flanking region of the eNOS gene by PCR, and the restriction enzyme MspI; and a kit for diagnosing a coronary artery spasm-associated disease, which comprises an amplification oligonucleotide for amplifying a portion encompassing the −1468 position in the 5'-flanking region of the eNOS gene by PCR, and the restriction enzyme MboI. It should be noted that the amplification oligonucleotide contained in the kit of the present invention includes oligonucleotides other than those listed in hereinafter Table 1, and can be selected among any oligonucleotides by reference to the genome sequence of eNOS.

In one aspect, the present invention relates to a method for diagnosing a coronary artery spasm-associated disease, which comprises detecting the presence of any one or more nucleotide changes in the eNOS gene as defined above which are responsible for the coronary artery spasm-associated disease.

BRIEF DESCRIPTION OF DRAWINGS

FIG. 1 is a photograph which shows the result of the electrophoresis obtained by PCR-SSCP analysis of DNA fragments containing exon 7 in the eNOS gene. Array indicates the shift of the bands.

FIG. 3A is a restriction map thereof. FIG. 3B is a photograph which shows the result of the real electrophoresis.

DETAILED DESCRIPTION OF THE INVENTION

Figure 2:
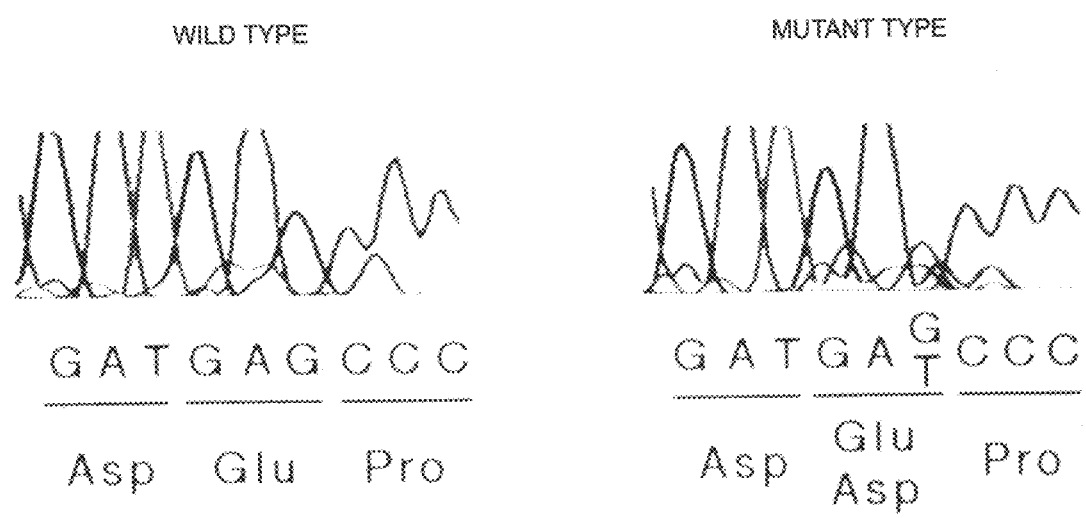
FIG. 2 is a graph which shows the result of the direct sequencing of the DNA fragments containing exon 7 in the eNOS gene originated from both cases with (mutant type) and without the mutation (wild type). The mutant type represents the heterozygote.

As stated above, the present inventors have focused on the eNOS gene, examined if the gene is responsible for the development of coronary spasm, and discovered the following findings:

A) Mutations in exons of the eNOS gene
1) Mutation in exon 7: guanine (G) at position 894 of the cDNA encoding eNOS is mutated to thymine (T)
By means of PCR-SSCP (polymerase chain reaction—single-strand conformation polymorphism) method and direct sequencing method, a point mutation was identified in exon 7 of the eNOS gene obtained from the patient having coronary spastic angina. The mutation represents change from GAG to GAT, and it corresponds to mutation of the amino acid residue from glutamic acid to aspartic acid (Glu298Asp). By screening of 96 patients having coronary spastic angina and 86 controls for this mutation, it was found that 22 patients and 7 controls carry this mutation, respectively.

2) Mutation in exon 6: cytosine (C) at position 774 of the cDNA encoding eNOS is mutated to thymine (T)
PCR-SSCP method revealed that this base substitution was found in four patients having coronary spastic angina among ten patients. On the other hand, this base substitution was not found in 9 controls (P=0.03). This base substitution is not accompanied with amino acid change.

B) Mutations in the 5'-flanking region of the eNOS gene
Several mutations were found in the 5'-flanking region of the eNOS gene, and the relationship between these mutation and coronary spastic diseases was evaluated to obtain the following results.

1) Thymine (T) in the 5'-flanking region (−786) is mutated to cytosine (C)
PCR-SSCP method revealed that this base substitution was found in 34 patients having coronary spastic angina among 123 patients (27.6%), while this base substitution was found in only 4 controls among 86 controls (4.7%) (P<0.0001).

2) Adenine (A) in the 5'-flanking region (−922) is mutated to guanine (G)
PCR-SSCP method revealed that this base substitution was found in 31 patients having coronary spastic angina among 104 patients (29.1%), while this base substitution was found in only 3 controls among 83 controls (3.6%) (P<0.0001).

3) Thymine (T) in the 5'-flankin region (−1468) is mutated to adenine (A)
PCR-SSCP method revealed that this base substitution was found in 26 patients having coronary spastic angina among 98 patients (26.5%), while this base substitution was not found in 26 controls (0%) (P<0.0006).

The above mutations associated with the eNOS gene are useful in diagnosis of coronary spasm-associated diseases.

The term "coronary spasm-associated disease(s)" in the present specification includes angina, in particular coronary spastic angina, variant angina, unstable angina, effort angina, rest angina, acute myocardial infarction, microvasulor disease, and the like.

The relationship between the coronary spasm and the mutations associated with the eNOS gene has been demonstrated by the present invention, and therefore, when the mutations in the eNOS gene or in the 5'-flanking region thereof which is obtained from a patient suspected to have coronary spasm-associated diseases is detected, it can estimate that the patient in question may have the risk factor of the coronary spasm-associated diseases. Only one of these mutations is sufficient for an indicator for the diseases, and two or more mutations may be better indicator. Further, it has been found that detection of the mutations both in the eNOS gene region and the 5'-flanking region thereof lead estimation that coronary spasm-associated diseases be severe.

As shown above, the present invention provides a process for screening for a gene involving a coronary artery spasm-associated disease, which comprises detecting the presence of one or more nucleotide changes in the gene of endothelial nitric oxide synthase (eNOS), which changes are selected from a group consisting of the changes from guanine (G) to thymine (T) at position 894 and from cytosine (C) to thymine (T) at position 774 of the cDNA sequence of the eNOS gene, and the changes from thymine (T) to cytosine (C) at position −786, from adenine (A) to guanine (G) at position −922 and from thymine (T) to adenine (A) at position −1468 of the 5′-flanking region of the eNOS gene, as well as the changes at the corresponding positions in the complementary strand thereof.

The term "the changes at the corresponding positions in the complementary strand thereof" means, for example in the case of the nucleotide change from guanine (G) to thymine (T) at position 894 in cDNA of the eNOS gene, then the change wherein cytosine (C) at the position in the complementary strand corresponding to the 894 position is mutated to adenine (A).

First, the method for obtaining the eNOS gene and the 5′-flanking sequence from a patient is outlined as below.

All biopsy can be used as a sample for obtaining the gene, and typically a white blood cell sample, and additionally biopsy of liver also can be used. The sample is treated with proteinase K-SDS to effect proteolysis and denaturation, and then extracted with phenol/chloroform to give genomic DNAs(+RNAs). If desired, the RNAs can be removed by RNase.

Then, PCR is performed using any one of the primers as shown below to amplify the genomic DNA. Then, the presence of the mutations is confirmed by the following procedure for detection of nucleic acid mutation.

1) RFLP method (restriction fragment length polymorphism)
2) PCR-SSCP method (single-stranded DNA conformation polymorphism analysis)
3) ASO hybridization method (allele specific oligonucleotide hybridization)

The PCR products are blotted on a support such as a nylon filter, and hybridized with a synthetic oligonucleotide probe of about 18-mers having a base sequence containing the mutation to be detected, which may be labeled with a radioisotope or biotin to give a signal. Then, when the filter is washed according to a Tm value of the probe, it is possible to detect a mismatch of one base pair, since the mismatch would make the hybrid melted. This method is typical as a method for detecting a specific mutation of base by PCR.

4) Sequencing method
5) Southern blot method

This is the typical method for detecting mutations which comprises digesting a DNA with a restriction enzyme, developing over electrophoresis, and hybridizing with a probe. This method includes both genomic Southern blot and PCR Southern blot methods. The latter, which uses the same principle as the method (3) is advantageous in accuracy in that it can provide information of migration.

6) ARMS (amplification refracting mutation system)

In PCR, a primer anneals to a template DNA, and then, a DNA polymerase produces a complementary DNA from 5′ to 3′ end. ARMS is based on the principle that amplification efficacy of PCR is decreased and the PCR products cannot be detected on gel electrophoresis when the 3′-end of the primer makes mismatch to the template DNA. When the primer having a mutation to be detected at its 3′-end is used in amplification of PCR, it is possible to detect the mutation by examining the presence or the absence of the amplified products.

7) DGGE (denaturing gradient gel electrophoresis)

This method is based on the principle that a heteroduplex containing a mismatch in PCR products may dissociates more readily than a homoduplex. In this method, a double-stranded DNA containing a mismatch, i.e., a mutation, is detected as migration on the electrophoresis gel for the reason that migration of such DNA is poor on the gel in the course of dissociation, which is further accelerated by elevating the density gradient of an urea and formamide in the developing polyacrylamide gel.

8) RNase A cleavage method

RNase A (ribonuclease) is an enzyme which does not decompose a double-stranded RNA or an RNA/DNA hybrid, and selectively decomposes a single-stranded RNA. So, when an RNA probe labeled with 32P is hybridized with a sample DNA which have been denaturated into a single-stranded, the hybrid is treated with RNase A, and the products are developed over electrophoresis, then two bands may be detected for reason that single-stranded RNA derived from the RNA probe hybridized with the mutant DNA is cleavaged by RNase A.

9) Chemical cleavage method

"C" nucleotide and "T" nucleotide in the mismatch site of a hybrid DNA are modified by hydroxylamine and osmium tetra-oxide, respectively, and then the modified DNA is treated with piperidine to cleavage the sugar residue. A hybrid of a labeled probe and the sample DNA is applied to this procedure, and developed over electrophoresis. When the mutation is present in the sample DNA, the labeled probe is detected in smaller size. In the case of detection of Glu298Asp, the mismatch site is C-T, and therefore the reverse sequence of the wild type also can be used for detecting the mismatch.

10) ligase method

This method is based on the principle that two kinds of oligonucleotides can not be ligated each other with DNA ligase when the template DNA has mismatch(es) at the binding site.

i) LMGD (ligase-mediated gene detection)

For example, one oligo DNA is labeled with 32P, while the other DNA is labeled with biotin. Both are ligated each other and the ligated product is collected by absorption to streptavidin. When they safely ligate each other, in other words, any mismatch is not formed, then they can be detected since radioactivity of 32P becomes higher.

ii) LCR (ligase chain reaction)

By repeating the above ligation except of using thermostable ligase, an oligo DNA is annealed with a DNA strand, similarly to in PCR, and therefore higher sensitive detection of the mutation is facilitated.

BEST MODE FOR CARRYING OUT THE INVENTION

1. Mutation in exon 7

The mutation in exon 7, specifically the mutation from guanine (G) to thymine (T) at position 894 of the cDNA encoding eNOS represents change from GAG to GAT, both which form the different restriction sites. So, the presence of the mutation can be determined using a restriction enzyme. Specifically, digestion of the amplified products with either the restriction enzyme BanII or MboI enables to detect the presence of the mutation. More specifically, the mutation is found to be present when the restriction enzyme BanII can cleavage the site in question, while the mutation is found to be absent when the restriction enzyme MboI can cleavage the site in question.

Alternatively, since the mutation from guanine (G) to thymine (T) at position 894 of the cDNA encoding eNOS corresponds to the mutation in the amino acid from glutamic acid to aspartic acid (Glu298Asp), the change of the amino acid sequence of eNOS, i.e., the change from glutamic acid to aspartic acid at position 298 of the amino acid sequence of eNOS may be an indicator.

2. Mutation in exon 6

The mutation in exon 6, specifically the mutation from cytosine (C) to thymine (T) at position 774 of the cDNA encoding eNOS gives different restriction site each other, so the presence of the mutation can be determined using a restriction enzyme. Specifically, digestion of the amplified products with the restriction enzyme FokI enables to detect the presence of the mutation. More specifically, the mutation is found to be present when the products can be digested with the restriction enzyme FokI, while the mutation is found to be absent when the products cannot be digested with FokI.

3. Mutation at position −786 in the 5'-flanking region

The mutation in the 5'-flanking region of the eNOS gene, specifically the mutation from thymine (T) to cytosine (C) at position −786 also gives different restriction site each other, so the presence of the mutation can be determined using a restriction enzyme. Specifically, digestion of the amplified products with the restriction enzyme MspI enables to detect the presence of the mutation. More specifically, the mutation is found to be absent when the restriction enzyme MspI cleaves the amplified products on one site, while the mutation is found to be present when MspI cleaves the amplified products on two sites.

4. Mutation at position −1468 in the 5'-flanking region

The mutation in the 5'-flankin region of the eNOS gene, specifically the mutation from thymine (T) to adenine (A) at position −1468 also gives different restriction site each other, so the presence of the mutation can be determined using a restriction enzyme. Specifically, digestion of the amplified products with the restriction enzyme MboI enables to detect the presence of the mutation. More specifically, the mutation is found to be absent when the restriction enzyme MboI cleaves the amplified products on one site, while the mutation is found to be present when MboI cleaves the amplified products on two sites.

EXAMPLES

Example 1

Detection of the mutation in exon 7 in the eNOS gene

Subjects are 96 patients having coronary spastic angina and 86 controls. All of the patients having coronary spastic angina undergo spontaneous stroke at rest (male 53, female 43, mean age 61, ages 33–86). Heart catheter examination has been performed on all patients to confirm coronary spasm induced by acetylcholine or ergonovine over coronary arteriography, as well as to confirm significant ST-T change over electrocardiogram (7,8). Significant constriction in coronary artery were not found in all patients (>75%).

Among 86 controls, 61 construct a breast pung group, 12 construct a group which is abnormal in electrocardiogram, and 13 construct a group Coronary arteriography revealed that no one in the controls has significant constrictions. When coronary spasm-inducing test was performed on 61 subjects of the breast pung group and 12 subjects of the group which is abnormal in electrocardiogram by coronary dosage of acetylcholine or ergonovine, all subjects are negative. The control does not include subjects having myocardial infarction, syndrome X, myocardiopathy, and cardiac insufficiency.

(1) Examination of the eNOS gene mutation bu. PCR-SSCP i) Isolation of DNA

Peripheral venous blood was collected from 10 patients having typical coronary spasm and 9 controls, and the DNAs were extracted from the white blood cells (28), using DNA extraction kit DNAQUICH [DAINIPPON SEIYAKU].

ii) PCR step

Referring to the structure of the eNOS gene which has been reported (18–25), PCR-SSCP method was performed on all exons in the eNOS gene (29).

All primers were prepared on the basis of the sequence of introns to flank each exon. All primers used in this step are shown in Table 1.

TABLE 1

Primers for all 26 exons of endothelial cell nitric oxide synthase (eNOS) gene used for polymerase chain reaction - single-strand conformation polymorphism (PCR-SSCP)

```
1.  5'-CAGCAGAGTGGACGCACAGTAAC  (SEQ ID NO: 3)      15. 5'-GTGACAACCTTGTCTTTGTCC (SEQ ID NO: 31)
    5'-TTGTTGCCCACCTGCTCCTAGCTG (SEQ ID NO: 4)          5'-TCGTCAGTGGAGCTCCCTTT  (SEQ ID NO: 32)
    (217)                                               (231)

2.  5'-AACCCTTCCTGATGACCCTATCCC (SEQ ID NO: 5)      16. 5'-AAAGGGAGCTCCACTGACGA  (SEQ ID NO: 33)
    5'-CTTACCCACCCTTTCCCTGGAGAC (SEQ ID NO: 6)          5'-AGAATCAGGGCAGAGTGAGG  (SEQ ID NO: 34)
    (200)                                               (284)

3.  5'-TCCTGACCTTTGCACTCCCTCGA  (SEQ ID NO: 7)      17. 5'-AGCAAGACGCAGTGAAGCCG  (SEQ ID NO: 35)
    5'-ATGGGAAGGTCGTCACGGGGTTTC (SEQ ID NO: 8)          5'-TGGCCCCAGAGTGCTTTAGT  (SEQ ID NO: 36)
    (250)                                               (275)

4.  5'-ACAACTTCCTGCTTGTCCCCTTCC (SEQ ID NO: 9)      18. 5'-ACTAAAGCACTCTGGGGCCA  (SEQ ID NO: 37)
    5'-ACCCCGCTCCCCTTTTGGTA     (SEQ ID NO: 10)         5'-AGGGTCAGGGTGTTCAGGACA (SEQ ID NO: 38)
    (259)                                               (203)

5.  5'-TCTGGAGCTGATACTCAAGACCC  (SEQ ID NO: 11)     19. 5'-TGTCCTGAACACCCTGACCCT (SEQ ID NO: 39)
    5'-CGCATGGGGAAAGAGCTGGTCAGA (SEQ ID NO: 12)         5'-GCTGGTGTGCCCTGTTGCTT  (SEQ ID NO: 40)
    (246)                                               (322)

6.  5'-TCTGACCAGCTCTTTCCCCATGCG (SEQ ID NO: 13)     20. 5'-CTCCCTGTGCACTATCCCCA  (SEQ ID NO: 41)
    5'-CCACTGGTTTCCTCATTCTCCACC (SEQ ID NO: 14)         5'-TCTAGCCCCTGTGCCTCATT  (SEQ ID NO: 42)
    (232)                                               (329)

7.  5'-AAGGCAGGAGACAGTGGATGGA   (SEQ ID NO: 15)     21. 5'-TCCAACCCACTGCATCCTGC  (SEQ ID NO: 43)
    5'-CCCAGTCAATCCCTTTGGTGCTCA (SEQ ID NO: 16)         5'-TGCTCCTGCTTGTTGCCTCA  (SEQ ID NO: 44)
    (248)                                               (259)
```

TABLE 1-continued

Primers for all 26 exons of endothelial cell nitric oxide synthase (eNOS)
gene used for polymerase chain reaction - single-strand conformation polymorphism (PCR-SSCP)

| | | | | | |
|---|---|---|---|---|---|
| 8. | 5'-GCTGATCCCACACCCCAACA<br>5'-TGCCTTGGACAGGTGCATTC<br>(250) | (SEQ ID NO: 17)<br>(SEQ ID NO: 18) | 22. | 5'-TGAGGCAACAAGCAGGAGCA<br>5'-CACCAAGTCTTCCATCTCAC<br>(202) | (SEQ ID NO: 45)<br>(SEQ ID NO: 46) |
| 9. | 5'-TGATCACCTCTGTCCCTACCGA<br>5'-ATGCAAACCCTTTGCCTTCCTG<br>(189) | (SEQ ID NO: 19)<br>(SEQ ID NO: 20) | 23. | 5'-ATGGAGTGTCTCTCCTGCCA<br>5'-TTCAGGCAGTCCTTTAGTGC<br>(173) | (SEQ ID NO: 47)<br>(SEQ ID NO: 48) |
| 10. | 5'-AAGAATGGGCGAGGTCTGTGGGT<br>5'-CAGGGGCTGCTTAGAATTAGAGC<br>(311) | (SEQ ID NO: 21)<br>(SEQ ID NO: 22) | 24. | 5'-AGAAGAGCCTTCCCAACCCG<br>5'-ATCTTCAGGTTACCATTGCG<br>(219) | (SEQ ID NO: 49)<br>(SEQ ID NO: 50) |
| 11. | 5'-TCCCTCCCAACCCATCATCTCTCT<br>5'-AGTGGTAGGCCCAGAACACTGCT<br>(208) | (SEQ ID NO: 23)<br>(SEQ ID NO: 24) | 25. | 5'-CAGACCTACGTGCAGGACAT<br>5'-ACCTTAGCAGGAACCCCGCA<br>(276) | (SEQ ID NO: 51)<br>(SEQ ID NO: 52) |
| 12. | 5'-CAGGACACCCTCACACCTTCCTCT<br>5'-TCTTTCTAGCTCCCTGCTCCC<br>(210) | (SEQ ID NO: 25)<br>(SEQ ID NO: 26) | 26-1. | 5'-GTTCTGATCCACTGTGCTCT<br>5'-TCTCCCGGAACTGGAAGGGA<br>(226) | (SEQ ID NO: 53)<br>(SEQ ID NO: 54) |
| 13. | 5'-ACAGCACCCAGGACATCTGTCTTC<br>5'-AGCCCCTTTCCTGGAAGTTCTCA<br>(163) | (SEQ ID NO: 27)<br>(SEQ ID NO: 28) | 26-2. | 5'-ACACCAACAGCCCCTGAGAG<br>5'-TGGCAGTAGGCCCTGGGGTA<br>(273) | (SEQ ID NO: 55)<br>(SEQ ID NO: 56) |
| 14. | 5'-TGATGTCAAACACTCCCCTCG<br>5'-AAAACGGACTTGAGGCACAG<br>(178) | (SEQ ID NO: 29)<br>(SEQ ID NO: 30) | 26-3. | 5'-TTAATCTGGAAGGCCCCTCC<br>5'-GAGGGAGACTCCGTTTCAAA<br>(267) | (SEQ ID NO: 57)<br>(SEQ ID NO: 58) |

Top: sense primer, bottom: antisense primer in each primer set. Base-pair length of amplified fragments in parentheses. Three primer sets were used in the analysis of exon 26.

To a solution in a total volume of 5 μl containing 50 mmol/L KCL, 20 mmol/L Tris-HCL (pH 8.4), 0.75 mmol/L MgCl$_2$, 0.1 mmol/L dNTPs, 0.2 ml α-[$^{32}$P]dCTP (0.2 ml), 5 pmol each primer, and 0.01U Taq polymerase (GIBCO BRL, Life Technologies Inc., MD USA) in each tube was added 30 ng of DNA from the patients.

PCR procedure was performed as follows: one cycle of 2 minutes at 94° C.; 30 cycles of 30 seconds at 94° C., 30 seconds at 55–58° C., and one minute at 72° C.; and the resulting amplified products were stored at 4° C. Amplification of exon 7 was conducted at 57° C.

iii) SSCP step

Electrophoresis was performed under three conditions in which one is 5% glycerol gel at room temperature, and the others are 5% and 10% glycerol gel at 4° C.

The glycerol gels were prepared as follows:
1) preparing a 5% solution containing 49:1 of acrylamide and N,N'-methylene-bis-acrylamide.
2) preparing 0.5×TBE (10×TBE is diluted 20 times: 108 g of Tris(hydroxymethyl)aminomethane+55 g of boric acid+40 ml of 0.5 M EDTA+a water of which volume makes a total volume 500 ml).
3) preparing a gel by adding 160 μl of 10% APS (ammonium peroxodisulfide) and 60 μl of TEMED (N,N,N',N'-tetramethylethylenediamine) to a solution of 5% or 10% glycerol.

iv) Result

Figure 1:
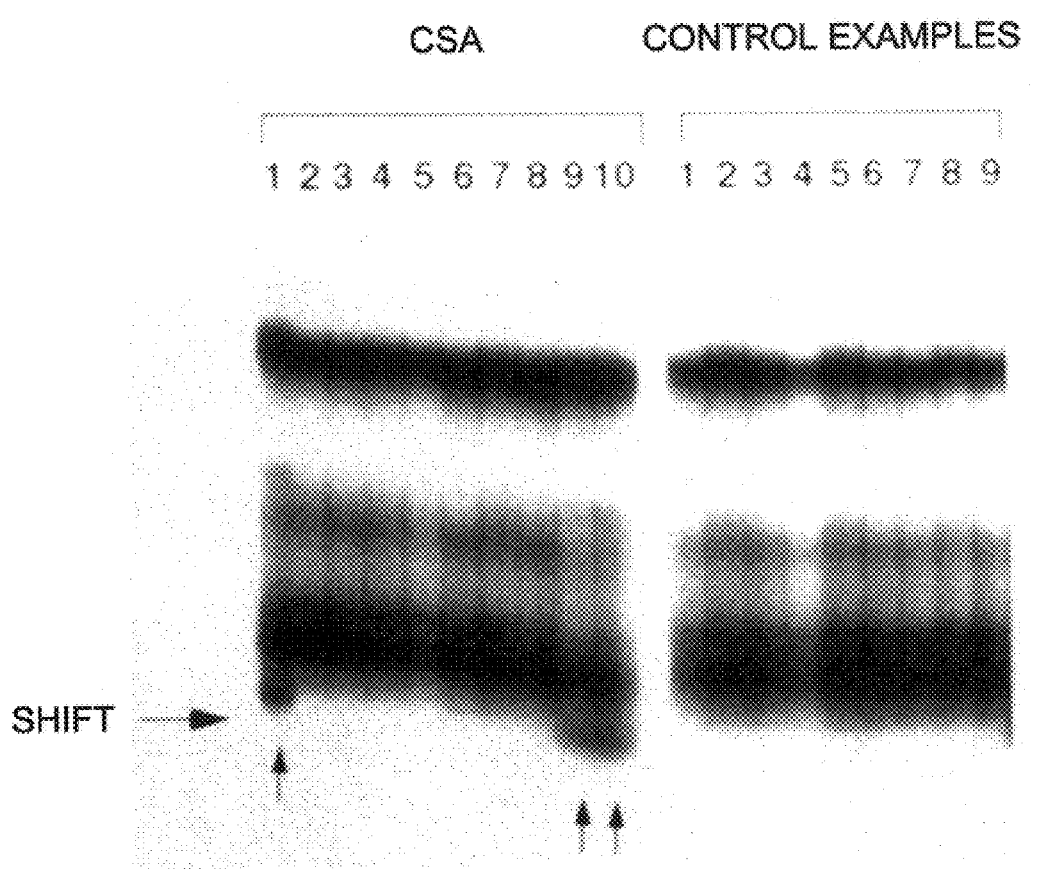

The result obtained by the amplification of exon 7 is shown in FIG. 1. This demonstrates a band-shift of the fragment comprising exon 7 in three of 10 coronary spastic angina patients. On the other hand, no shift was shown in controls.

(2) Analysis of the mutant gene by direct sequencing method

DNAs of the patients found to have the mutation and the controls found to have no mutation by PCR-SSCP in the step (1) were again amplified according to the same condition as that of the step (1), and the amplified products were purified by Wizard PCR Preps DNA purification system (Wizard PCR Preps DNA Purification System, Promega, USA). Then, the base sequence was determined by an autosequencer produced by ABI [USA].

By analysis of the mutant DNA and the wild DNA by direct sequencing method, point mutation from guanine (G) to thymine (T) at position 894 in exon 7 of the eNOS cDNA was found. This mutation was confirmed in three patients which had been found to have the mutation. The point mutation represents missense mutation which corresponds to the change from glutamic acid to aspartic acid (Glu298Asp). The result of the direct sequencing is shown in FIG. 2. This figure includes the results of the wild type without the mutation and the heterozygote type.

(3) Screening for the mutation from "G" to "T" by PCR-RFLP

After the missense mutation inducing Glu298Asp was found in exon 7 of the eNOS gene as shown in the step (2), all of 96 patients having coronary spastic angina and 86 controls were screened for the mutation. This screening was performed by PCR-RFLP (polymerase chain reaction—restriction fragment length polymorphism). Two types of the restriction enzyme, BanII and MboI (purchased from TAKARA) were used in order to prevent any mistakes based on the incomplete cleavage by restriction enzymes.

Exon 7 of the eNOS gene from all cases was amplified according to the procedures of (ii) in the step (1). The amplified fragments containing exon 7 spanned 248 bp. Then, the amplified fragments were digested with either BanII or MboI according to instructions of the manufacture. The digested products were elctrophoresed on 4% Nusieve GTG agarose gel to give a band.

Figure 3A:
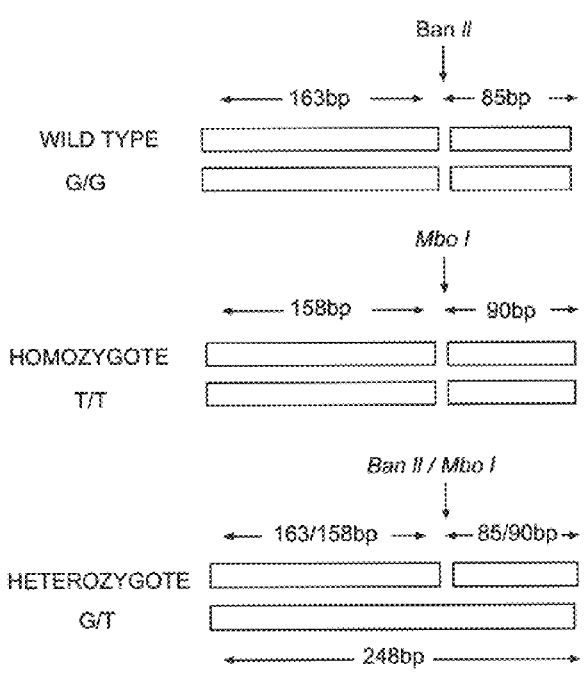
FIGS. 3A–3B are a result of the screening of the DNA fragments containing exon 7 in the eNOS gene by PCR-RFLP. The restriction enzyme is BanII and/or MboI.
Figure 3B:
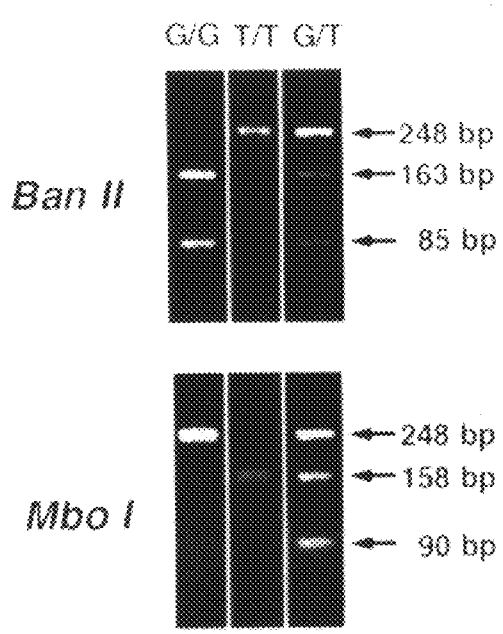

The results could be classified into three patterns as shown in FIG. 3. FIG. 3A is a restriction map, and FIG. 3B is a photograph of the result of the actual electrophoresis. As shown in FIG. 3B, BanII gives two fragments having 163 bp and 85 bp in length and MboI gives one band having 248 bp which is not cleavaged, in the wild type without the mutation. This demonstrates that the wild type with the mutation has one restriction site of BanII and no restriction site of MboI.

In the case of homozygote having T/T at position 894 of the eNOS cDNA, BanII gives no cleavage (248 bp), while MboI gives two fragments of 158 bp and 90 bp in length. This demonstrates that the homozygote has no restriction site of BanII, and one restriction site of MboI.

There are some cases which have given three bands of 248 bp, 163 bp and 85 bp in length by BanII, and 248 bp, 158 bp and 90 bp in length by MboI. This is regarded as to the heterozygote (G/T) since each BanII and MboI merely gives one cleavage site in either band.

On the basis of the three patterns as shown above, frequency of the eNOS gene Glu298Asp mutation was examined on all cases of the coronary spastic angina and control groups. Digestion with both enzymes was performed on all cases. The results obtained by using these two enzymes are consistent among all cases.

Glu298Asp mutation was found in 22 of 96 coronary spastic angina patients (23%), in which one is the homozygote and 21 are the heterozygote. On the other hand, the mutation was found in 7 of 86 controls (8%), all of which are the heterozygote.

(4) Statistic analysis: relationship between coronary spasm and Glu298Asp mutation or other risk factors The mutation frequency obtained in the step (3) was compared with frequency of other coronary risk factors including age, sex, high blood pressure, diabetus melitus, haypercholesterolemia, body mass index and smoking between the control and coronary spastic angina groups by Chi-square analysis and unpaired t-test with Fisher's exact probability. Further, multivariate analysis (multiple logistic regression analysis) was performed to examine whether factor is mostly associated with the coronary spasm by SPSS Advanced Statistics 6.1 for the Macintosh (SPSS Japan Inc., Japan). Dummy variables were used as all independent variables as follows. Each numerical value represents means±SD.

Sex; 0: male, 1: female

Age; 0: under 60, 1: 60 or above

Body mass index; 0: under 26, 1: 26 or above

Cholesterolemia; 0: normal, 1: Haypercholesterolemia (threshold, 260 mg/dl)

Smoking; 0: nonsmoker, 1: smoker

Hypertension; 0: normal, 1: high (threshold, 160/95 mmHg)

Diabetus melitus; 0: absent, 1: present (threshold, 140 mg/dl of fasting blood glucose or 200 mg/dl in OGTT)

The results of Chi-square analysis and the results of analysis using forward stepwise selection (Wald) are shown in Tables 2 and 3, respectively, wherein p=0.05 is regarded as a significant value in statistics.

Results of the statistic analysis

Of the relationships between coronary spasm, and Glu298Asp mutation or other risk factors such as age, sex, high blood pressure, diabetes melitus, hypercholesterolemia, body mass index and smoking, sex (p=0.035), smoking (p=0.00001) and Glu298Asp mutation (p=0.005) were significant as shown in Table 2.

TABLE 2

Clinical characteristics of the study patients; comparison between the control and coronary spastic angina groups

|  | Control n = 86 | Spasm n = 96 | p value |
| --- | --- | --- | --- |
| Age | 61 ± 12 | 61 ± 11 | .97* |
| Men:Women | 35:51 | 53:43 | .035** |
| Body mass index | 23.4 ± 3.7 | 23.1 ± 3.0 | .48* |
| High blood pressure | 29/85 | 35/94 | .39** |
| Diabetus melitus | 15/84 | 10/93 | .13** |
| Hypercholesterolemia | 31/82 | 31/93 | .32** |
| Smokers | 17/84 | 50/95 | .00001** |
| Glu298Asp mutation | 7/86 | 22/96 | .005** |

*Unpaired t-test and **Chi-square analysis with Fisher's exact probability were performed.

The results of multivariate analysis (multiple logistic regression analysis) is shown in Table 3. Table 3 shows that smoking is the first factor, which shows the responsibility for coronary spasm (p=0.0005), and Glu298Asp mutation is the second factor (p=0.0272). Multiple logistic regression analysis does not show any significant relationship between sex and coronary spasm.

TABLE 3

Parameters associated with coronary spastic angina by multiple logistic aegression analysis; final variables in the equation using forward stepwise regression analysis (Wald)

| Variable | β | SE | Wald | df | Significance | R | Exp (β) |
| --- | --- | --- | --- | --- | --- | --- | --- |
| Smoking | 1.2342 | .3529 | 12.2316 | 1 | .0005 | .2120 | 3.4355 |
| Glu298Asp | 1.0746 | .4866 | 4.8771 | 1 | .0272 | .1124 | 2.9288 |
| Constant | −.4371 | .2139 | 4.1747 | 1 | .0410 | — | — |

Example 2

Detection of the mutation in exon 6 of the eNOS gene

According to the procedures of Example 1, genomic DNA was isolated from 10 coronary spastic angina patients and 9 controls. PCR was performed using the primers described in Table 1, and then SSCP procedure was performed to detect the mutation in exon 6. Then, the exon 6 was sequenced directly to identify the substitution of the base from cytosine (C) to thymine (T) at position 774 in the cDNA of the eNOS gene.

This substitution of the base was found in 4 of 10 patients having coronary spastic angina, while this substitution was not found in 9 controls (p=0.03). This substitution is not associated with any change of amino acid.

Example 3

Detection of the mutation in the 5'-flanking region of the eNOS gene (1)

The procedures of Example 1 were substantially repeated except using the following primers, to identify the substitution of the base from thymine (T) to cytosine (C) in the 5'-flanking region (−786).

PCR-SSCP(−585~−820 bp; 236 bp)

5' side primer: 5'-ATGCTCCCACCAGGGCA TCA-3' (SEQ ID NO. 59)

3' side primer: 5'-GTCCTTGAGTCTGACATTA GGG-3' (SEQ ID NO. 60)

This substitution of the base was found in 34 of 123 patients having coronary spastic angina (27.6%), while this substitution was found in only 4 of 86 controls (4.7%). (P<0.0001)

Example 4
Detection of the mutation in the 5'-flanking region of the eNOS gene (2)

The procedures of Example 1 were substantially repeated except using the following primers, to identify the substitution of the base from adenine (A) to guanine (G) in the 5'-flanking region (−922).

PCR-SSCP(−801∼−1008 bp; 208 bp)

5' side primer: 5'-TCAGTCTCTGAGGTCTC
GAA-3'  (SEQ ID NO. 61)

3' side primer: 5'-TGATGCCCTGGTGGGAG
CAT-3'  (SEQ ID NO. 62)

This substitution of the base was found in 31 of 104 patients having coronary spastic angina (29.1%), while this substitution was found in only 3 of 83 controls (3.6%). (P<0.0001)

Example 5
Detection of the mutation in the 5'-flanking region of the eNOS gene (3)

The procedures of Example 1 were substantially repeated except using the following primers, to identify the substitution of the base from thymine (T) to adenine (A) in the 5'-flanking region (−1468).

PCR-SSCP(−1214∼−1490 bp; 221 bp)

5' side primer: 5'-CCATTAACTGGAACCTAG
GAA-3'  (SEQ ID NO:63)

3' side primer: 5'-AGCCTGGGCTTTGTCCCA
TGA-3'  (SEQ ID NO:64)

This substitution of the base was found in 26 of 98 patients having coronary spastic angina (26.5%), while this substitution was not found in 26 controls (0%). (P<0.0006)

Example 6
Screening for the mutations

The five mutations identified in the above working examples can be screened in a large way by ASO hybridization (Hybridization with Allelic-Specific Oligonucleotides) method, for example. This ASO hybridization method for extensive screening is illustrated below:
1) performing PCR similarly to SSCP. In this case, the final volume is 20 μl. Composition of the reaction and cycle condition are the same as those in Example 1;
2) taking a 10 μl aliquot of the PCR reaction, immobilizing a 100 μl aliquot of 200 μl of 0.5 M NaOH (1.5 M NaCl+25 mM EDTA2Na) on a nylon membrane for the wild type, and then immobilizing the residual 100 μl on a nylon membrane for the mutant type;
3) packing each of the immobilized nylon membranes into the different hybribag, adding the pre-hybridization solution (3×SSPE, 5×Denhart's regent, 0.5% SDS, 1 μg/μl herring sperm DNA) to the bags, and incubating the bags at 65° C. for two hours;
4) introducing the normal probe labeled with $^{32}$P ($5\times10^6$ dpm/ml) and the abnormal probe without any labels in five times volume into one bag, while introducing the abnormal probe labeled with $^{32}$P ($5\times10^6$ dpm/ml) and the normal probe without any labels in five times volume into the other bag;
5) incubating each of bags at 60° C. for 30 minutes, and further incubating the same for additional one hour as decreasing the temperature from 60° C. to X° C. wherein X is 53 in Example 3, 50 in Example 4, 46 in Example 5;
6) taking the nylon membranes out of the bags, and incubating the membranes twice in 2×SSPE (0.1% SDS) at room temperature for 10 minutes, and then incubating them once in 5×SSPE (0.1% SDS) at X° C. for 10 minutes.
7) wrapping the nylon membranes with saran wrap, overlaying them onto X-ray film, and developing the X-ray film (autoradiography).

Example 7
Screening for the mutations in exon 6 and the 5'-flanking region of the eNOS gene By direct sequencing method described in Examples 2, 3 and 5, the substitution of the base from cytosine (C) to thymine (T) at position 774 in the cDNA of the eNOS gene, as well as the substitutions from thymine (T) to cytosine (C) at position −786 and from thymine (T) to adenine (A) at position −1468 in the 5'-flanking region of the eNOS gene were identified. Screening for these mutations was performed by PCR-RFLP method. Oligonucleotides and conditions for the amplification in this PCR are shown in Tables 4 and 5:

TABLE 4

Base Sequence of Oligonucleotides for PCR Amplification (a) exon 6
(SEQ ID NO:65)
5'-TCTGACCAGCTCTTTCCCCATTCG-3' (sense)

(SEQ ID NO:66)
5'-CCACTGGTTTCCTCATTCTCCACC-3' (anti-sense)

(b) 5'-flanking region (-1468)
(SEQ ID NO:67)
5'-CTCCAGCCCCTCAGATGA-3'   (anti-sense 1)

(SEQ ID NO:68)
5'-TCCAGCCCCTCAGATGG-3'   (anti-sense 2)

(SEQ ID NO:69)
5'-GTCCTTGAGTCTGACATTAGGG-3'   sense)

(c) 5'-flanking region (-786)
(SEQ ID NO:70)
5'-AATGAGTCATCCTTGGTCATG-3'   (anti-sense)

(SEQ ID NO:71)
5'-GGGTTTGTAGTTCTGTGT-3'   (sense 1)

SEQ ID NO:72)
5'-GGGTTTGTAGTTCTGTGC-3'   (sense 2)

TABLE 5

| | PCR amplification conditions | | | | | | |
|---|---|---|---|---|---|---|---|
| | temperature (° C.) | | | time* (seconds) | | | |
| region for amplification | De.[1] | An.[2] | Ex.[3] | De.[1] | An.[2] | Ex.[3] | cycle |
| exon 6 | 94 | 63 | 72 | 60 | 60 | 60 | 32 |
| 5'-flanking region | 94 | 58 | 72 | 45 | 75 | 60 | 32 |
| 5'-flanking region | 94 | 60 | 72 | 45 | 75 | 60 | 32 |

PCR reaction was performed in a volume of 25 ml of buffer (composition: 10 mM Tris-HCl pH 9.0, 50 mM KCl, 1.5 mM MgCl$_2$, and 0.1% Triton X-100; 0.5 mM each of the PCR primers; 200 mM deoxynucleotide; 0.5 U Taq polymerase).
*: Temperature was controlled on a DNA Thermal Cyclar 480 (Perkin-Elmer Cytus).
De.[1]: denaturation; An.[2]: annealing; Ex.[3]: extension (1) Mutation in exon 6

Figure 4:
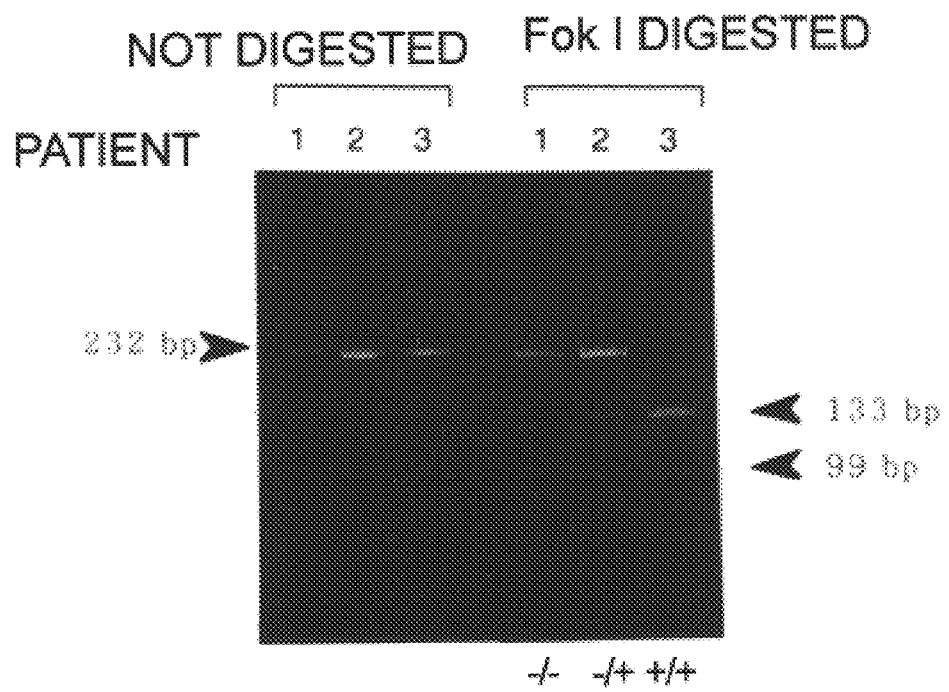
FIG. 4 is a photograph which shows the result of the electrophoresis obtained by PCR-RFLP for screening the DNA fragments containing exon 6 in the eNOS gene. The restriction enzyme is FokI.

According to the procedures of the step (2) in Example 1, exon 6 of the eNOS gene in a sample was amplified using the primers described in Table 5 and the condition for amplification described in Table 5. The resulting amplified fragment (232 bp) was digested with FokI according to instructions of the manufacture, and the digested products were electrophoresed on 10% polyacrylamide gels to identify the bands. Since FokI can cleaves only mutant gene, it was found that the homozygote having C/C gives the band of 232 bp, the heterozygote having C/T gives the bands of 232 bp, 133 bp and 99 bp, and the homozygote having T/T gives the bands of 133 bp and 99 bp. The results of the screening by PCR-RFLP is shown in FIG. 4.

(2) The mutation at position −786 in the 5'-flanking region

Figure 5:
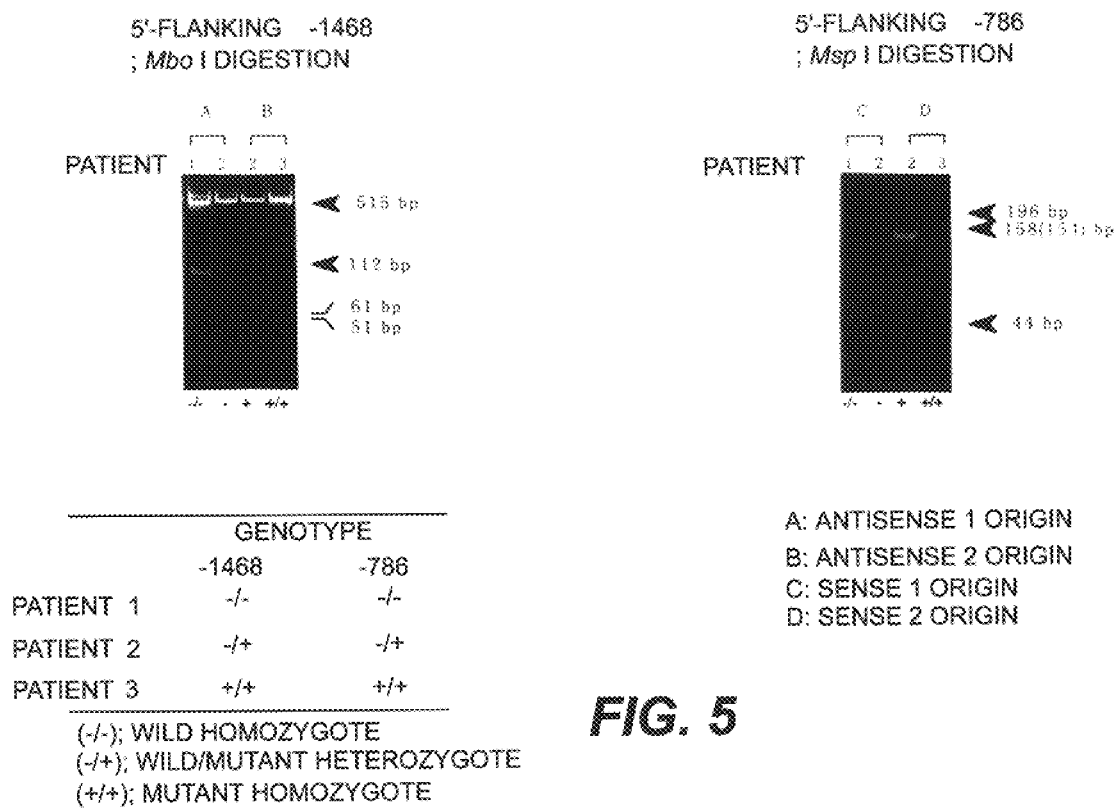
FIG. 5 is a photograph which shows the results of the electrophoresis obtained by PCR-RFLP for screening the DNA fragments containing the −786 and −1468 positions in the 5'-flanking region of the eNOS gene. The restriction enzyme is MspI in the case of the −786 mutation, while it is MboI in the case of −1468 mutation.

According to the procedures of the step (2) in Example 1, a portion encompassing the mutation at position −786 in the 5'-flanking region of the eNOS gene in a sample was amplified using the primers described in Table 5 and the condition for amplification described in Table 5. The resulting amplified fragment (354 bp) was digested with MspI according to instructions of the manufacture, and the digested products were electrophoresed on 10% polyacrylamide gels to identify the bands. MspI cleaves the homozygote of the wild type gene (T) at one site to give two bands of 196 bp and 158 bp. On the other hand, MspI cleaves the homozygote of the mutant gene (G) at two sites to give three bands of 158 bp, 154 bp and 44 bp. The results of the screening by PCR-RFLP is shown in FIG. 5.

(3) The mutation at position −1468 in the 5'-flanking region

According to the procedures of the step (2) in Example 1, a portion encompassing the mutation at position −1468 in the 5'-flanking region of the eNOS gene in a sample was amplified using the primers described in Table 5 and the condition for amplification described in Table 5. The resulting amplified fragment (627 bp) was digested with MboI according to instructions of the manufacturer, and the digested products were electrophoresed on 10% polyacrylamide gels to identify the bands. MboI cleavages the homozygote of the wild type gene (T) at one site to give two bands of 515 bp and 112 bp. On the other hand, MboI cleavages the homozygote of the mutant gene (A) at two sites to give three bands of 515 bp, 61 bp and 41 bp. The results of the screening by PCR-RFLP is shown in FIG. 5.

(4) The mutation at position −922 in the 5'-flanking region

This mutation was detected by PCR-SSP (Sequence-Specific Primer). Each of two types of primers for forward and backward extension (totally four species) were designed to extend from "A" or "G" at position −922 to 3' direction. These primers are the same as those described in (b) and (c) in Table 4. A sense and an anti-sense primers (two species) to be paired to these primers were designed so that the region to be amplified contains the mutation at position −1468 and −786, respectively. The PCR procedure revealed that the homozygote containing A/A at position −922 can be amplified by only primer having "A" or "T" (complementary sequence) at the 3' origin, while the homozygote containing G/G can be amplified by only primer having "G" or "C" (complementary sequence) at the 3'-side terminal.

The resulting amplified fragments are the same as those obtained in the above (2) and (3). By examination of the amplified fragments in some samples, it was found that the amplified fragment (354 bp) obtained in the above (2) which is derived from the allele having "A" at position −922 (wild type) gives only wild type having "T" at position −786, while the amplified fragment (354 bp) obtained in the above (2) which is derived from the allele having "G" at position −922 (mutant type) gives only mutant type having "G" at position −786. Similarly, the amplified fragment (627 bp) of the above (3) which is derived from the allele having "A" at position −922 (wild type) gives only wild type having "T" at position −1468, while the amplified fragment (627 bp) of the above (3) which is derived from the allele having "G" at position −922 (mutant type) gives only mutant type having "A" at position −1468. These findings show that in a certain embodiment that all of the above mutations in the 5'-flanking region may form a linkage to reside on the same allele, indicating that when either one of three mutations are detected, then the other two mutations can be present.

Discussion

As shown above, the present inventors have hypothesized that mutations in the eNOS gene should be responsible for a decrease of activities of NOS, which decrease may induce coronary spasm, and carried out some experiments for supporting our hypothesis. When the hypothesis is true, it is consistent with the fact that the coronary spasm does not occur only at one branch, but also at multiple branches (8). Mutation Glu298Asp as shown in Example 1 have been previously reported by Marsden, et. al. (24), but therein the significance of the mutation was not described.

In Example 1, the mutation Glu298Asp was found in 23% of the coronary spastic angina patients, while found in 8% of the controls, indicating that the frequency of the mutation in the angina group is significantly high compared with that in the control group. The result of the multivariate analysis shows that the relationship between the coronary spasm and the mutation Glu298Asp is regarded as significant.

It can be considered that since the rate of this mutation in the coronary spastic group is merely 23%, the coronary spasm of the residual 77% patients may be caused by pathogenic factors other than this mutation. The present inventors have hypothesized that mutations may exist in regions including the promoter and introns other than exon 7 of eNOS which is described in Example 1, and performed some experiments, so as to find the results to support our hypothesis (Examples 2–5). Accordingly, when the relationship of these mutations is more specifically examined, it is possible to lead to a more reliable diagnosis for coronary spasm-associated diseases.

Alternatively, it can be considered that the coronary spasm may be caused by not only the eNOS gene, but also other genes. Further, it should be noted that the coronary spasm may be caused by not only genetic factors, but also environmental factors, for the patients having the familial attack type of coronary spasm are relatively less. Smoking is shown to be one of the risk factors of the coronary spasm in Example 1. This result is consistent with the previous reports (30, 31). The results of the multiple logistic regression analysis in the present specification shows that the smoking is the most dominant factors among all risk factors including the mutation, indicating that the environmental factors are extremely important in pathogenesis of the coronary spasm. Other researchers also have indicated that the smoking causes endothelial damages (32, 33).

The mutation Glu298Asp has been found in 8% of the controls (786, Example 1). This reason is not fully understood, and it is noted, however, that since six subjects are non-smokers among seven subjects which have the mutation, these six subjects are unrelated to the smoking which is the strong risk factor. Difficulty in diagnosis of the coronary spasm also should be taken account. Specifically, the coronary spasm may be overlooked for some reasons, and the case which should have been assigned to the coronary spastic group is assigned to the control group for the following reasons:

1) The attack is liable to be overlooked because the attack often occurs midnight to early morning, and generally it dose not occur daytime;
2) Administration of acetylcholine into coronary artery cannot always induce coronary spasm, and the coronary spasm is often dependent on disease activity of coronary spastic angina.
3) Over two third attacks of coronary spasm is silent (subclinical);
4) Even if the result of examination does not show to be coronary spastic angina, the angina may occur in future. On the contrary, the coronary spastic angina group herein is population of the cases which have been definitely diagnosed to have the coronary spasm by coronary arteriography.

By the present invention, it is demonstrated that the coronary spasm is caused by genetic factors as well as environmental factors for the first time, and better diagnostic method for coronary spasm-associated diseases can be provided.

The literatures referred to herein are listed as following:

LITERATURES

1) Hillis L D, Braunwald E, Coronary-artery spasm. N Engl J Med. 1978; 299:695–702
2) Conti C R. Coronary artery spasm and myocardial infarction. N Engl J Med. 1983; 309:238–239
3) Yasue H, Omote S, Takizawa A, Nagao M. Coronary arterial spasm in ischemic heart disease and its pathogenesis. A review. Circ Res. 1983; 52 (Supple I):147–152
4) Maseri A, Davies G, Hackett D, Kaski J C. Coronary artery spasm and vasoconstriction. The case for a distinction. Circulation. 1990; 81:1983–1991
5) Yasue H, Nagao M, Omote S, Takizawa A, Miwa K, Tanaka S. Coronary artery spasm and Prinzmetal's variant form of angina induced by hyperventilation and tris-buffer infusion. Circulation. 1978; 58:56–62
6) Yasue H, Omote S, Takizawa A, Nagao M, Miwa K, Tanaka S. Circadianvariation of exercise capacity in patients with Prinzmetal's variant angina. Role of exercise-induced coronary artery spasm. Circulation. 1979; 59:938–948
7) Yasue H, Horio Y, Nakamura N, Fujii H, Imoto N, Sonoda R, Kugiyama K, Obata K, Morikami Y, Kimura T. Induction of coronary artery spasm by acetylcholine in patients with variant angina: possible role of the parasympathetic nervous system in the pathogenesis of coronary artery spasm. Circulation. 1986; 74:955–963
8) Okumura K, Yasue H, Horio Y, Takaoka K, Matsuyama K, Kugiyama K, Fujii H, Morikami Y. Multivessel coronary spasm in patients with variant angina: a study with intracoronary injection of acetylcholine. Circulation. 1988; 77:535–542
9) Moncada S, Palmer R M, Higgs E A. Nitric oxide: physiology, pathophysiology and pharmacology. Pharmacol Rev.. 1991; 43:109–142
10) Yasue H. Pathogenesis and clinical features of coronary spasm. J Jap Soc Intern Med 1995; 84:1407–1415
11) Bredt D S, Hwang P M, Glatt C E, Lowenstein C, Reed R R, Synder S H. Cloned and expressed nitric oxide synthase structurally resembles cytochrome P-450 reductase. Nature. 1991; 351:714–718
12) Nakane M, Schmidt H H W, Pollock J S, Forstermann U, Murad F. Cloned human brain nitric oxide synthase is highly expressed in skeletal muscle FEBS Let. 1993: 316:175–180
13) Lyons, C R, Orloff G J, Cunningham J M. Molecular cloning and functional expression of an inducible nitric oxide synthase from a murine macrophage cell line J Biol Chem. 1992; 267:6370–6374
14) Xie Q, Cho H J, Calaycay J, Mumford R A, Swiderek K M, Lee T D, Ding A, Troso T, Nathan C. Cloning and characterization of inducible nitric oxide synthase from mouse macrophage Science. 1992; 256:225–228
15) Lowenstein C J, Glatt C S, Bredt D S, Synder S H. Cloning and expressed macrophage nitric oxide synthase contrasts with the brain enzyme Proc Natl Acad Sci U.S.A. 1992; 89:6711–6715
16) Geller D A, Lowenstein C J, Shapiro R A, Nussler A K. Di Silvio M, Wang S C, Nakayama D K, Simmons R L, Snyder S H, Billiar T R. Molecular cloning and expression of inducible nitric oxide synthase from human hepatocytes. Proc Natl Acad Sci USA. 1993; 90:3491–3495
17) Chartrain N, Geller D, Koty P, Sitrin N, Nussler A, Hoffmann E, Billiar T, Hutchinson N, Mudgett J. Molecular cloning, structure, and chromosomal localization of the human inducible nitric oxide synthase gene. J Biol Chem. 1994; 269:6765–6772
18) Lamas S, Marsden P A, Gordon K L, Tempst P, Michel T. Endothelial nitric oxide synthase: Molecular cloning and characterization of a distinct constitutive enzyme isoform. Proc Natl Acad Sci. 1992; 89:6348–6352
19) Sessa, W C, Harrison J K, Barber C M, Zeng D, Durieux M E, D'Angelo D D, Lynch K R, Peach M J. Molecular cloning and expression of a c DNA encoding endothelial cell nitric oxide synthase J Bio Chem. 1992; 267:15274–15276
20) Nishida K, Harrison D G, Navas J P, Fisher A A, Docery S P, Uematsu M, Nerem R M, Alexander R W, Murphy T J. Molecular cloning and characterization of the constitutive bovine aortic endothelial cell nitric oxide synthase J Clin Invest. 1992; 90:2092–2096
21) Janssens S P, Shimouchi A, Quetermous T, Bloch D B, Bloch K D Cloning and expression of a cDNA encoding human endothelium-derived relaxing factor/nitric oxide synthase. J Biol Chem. 1992; 267:14519–14522
22) Marsden P A, Schappert K T, Chen H S, Flowers M, Sundell C L, Wilcox J N, Lamas S, Michel T. Molecular cloning and characterization of human endothelial nitric oxide synthase FEBS Lett. 1992; 307:287–293
23) Nadaud S, Bonnardeaux A, Lathrop G M, Soubrier F. Gene structure, polymorphism and mapping of the human endothelial nitric oxide synthase gene. Biochem Biophys Res Commun. 1994; 198:1027–1033
24) Marsden P A, Heng H H Q, Scherer S W, Stewart R J, Hall A V, Shi X M, Tsui L C, Schappert K T. Structure and chromosomal localization of the human constitutive endothelial nitric oxide synthase gene. J Biol Chem. 1993; 268:17478–17488
25) Miyahara K, Kawamoto T, Sase K, Yui Y, Toda K, Yang L X, Hattori R, Aoyama T, Yamamoto Y, Doi Y, Ogoshi S, Hashimoto K, Kawai C, Sasayama S, Shizuta Y. Cloning and structural characterization of the human endothelial nitric-oxide-synthase gene Eur J Biochem. 1994; 223:719–726
26) Yasue H, Kugiyama K. Coronary artery spasm: Japanese view. Coronaryartery disease. 1990; 1:668–673
27) Bertrand M E, LaBlanche J M, Tilmant P Y, Thieuleux F A, Delforge M R, Carre A G, Asseman P A, Berzin B, Libersa C, Laurent J M. Frequency of provoked coronary arterial spasm in 1089 consecutive patients undergoing coronary arteriography. Circulation. 1982; 65:1299–1306
28) Saiki R K, Scharf S, Faloona F, Mullis K B, Horn G T, Erlich H A, Arnheim N. Enzymatic amplification of β-globin genomic sequences and restriction site analysis for diagnosis of sickle ell anemia. Science. 1985; 230:1350–1354
29) Orita M, Suzuki Y, Sekiya T, Hayashi K. Rapid and sensitive detection of point mutation and DNA polymorphisms using the polymerase chain reaction. Genomics. 1989; 5:874–879
30) Dennis G. Caralis, Ubeydullah Deligonul, Morton J. Kern, Jerome D. Cohen. Smoking is a risk factor for coronary spas in young women. Circulation. 1992; 85:905–909
31) Sugiishi M, Takatsu F. Cigarette smoking is a major risk factor for coronary spasm. Circulation. 1993; 87:76–79
32) Celermajer D S, Sorensen K E, Georgakopoulos D, Bull C, Thomas O, Robinson J, Deanfield J E. Cigarette smoking is associated with dose-related and potentially reversible impairment of endothelium-dependent dilation in healthy young adults. Circulation. 1993; 88:2149–2155
33) Zeiher A M, Schachinger V, Minners J. Long-term sigarette smoking impairs endothelium-dependent coronary arterial vasodilator function. Circulation. 1995; 92: 1094–1100
34) Yasue H, Takizawa A, Nagao M, Nishida S, Horie M, Kubota J, Omote S, Takaoka K, Okumra K. Long-term prognosis for patients with variant angina and influential factors. Circulation. 78;1–9:1988
35) Egashira K et. al. Preserved Endothelium-dependent Vasodilation at the Vasospastic Site in Patients with Variant Angina. Endothelial Function and Coronary Vasospasm Vol. 89: 1047–1052:1992

We claim:

1. A process for screening for a gene involving a coronary artery spasm-associated disease, which comprises;

obtaining a DNA sample from a subject to be tested for a coronary artery spasm-associated disease; and detecting the presence of one or more nucleotide changes in a gene encoding human endothelial nitric oxide synthase (eNOS), which changes are selected from a group consisting of the changes in the eNOS cDNA sequence from guanine (G) to thymine (T) at position 894, and from cytosine (C) to thymine (T) at position 774 of SEQ ID NO:2, and the changes in the 5' flanking region of the human eNOS gene from thymine (T) to cytosine (C) at position 815, from adenine (A) to guanine (G) at position 679, and from thymine (T) to adenine (A) at position 133 of SEQ ID NO:1, and changes at the corresponding positions in the complementary strands thereof.

2. The process of claim 1 which comprises detecting the presence of two or more nucleotide changes selected from any one of nucleotide changes in the eNOS gene, and any one of nucleotide changes in the 5'-flanking region thereof.

3. The process of claim 1 or 2 in which the coronary artery spasm-associated disease is angina.

4. The process of claim 3 in which the coronary artery spasm-associated disease is coronary spastic angina.

5. The process of claim 1 in which the detection of the presence of the changes is performed by amplifying the relevant region to exon 7 in the cDNA coding eNOS by means of PCR, digesting the amplified fragments with the restriction enzyme(s) BanII and/or MboI, and electrophoresing the fragments digested with the enzyme.

6. A diagnostic coronary artery spasm-associated disease kit, which comprises;

a pair of amplification oligonucleotides for amplifying the relevant portion to exon 7 in SEQ ID NO:1 in the cDNA coding eNOS by PCR; and the restriction enzyme(s) BanII and/or MboI.

7. The process of claim 1 in which the detection of the presence of the changes is performed by amplifying the relevant region to exon 6 in the cDNA coding eNOS by means of PCR, digesting the amplified fragments with the restriction enzyme FokI, and electrophoresing the fragments digested with the enzyme.

8. A diagnostic coronary artery spasm-associated disease kit, which comprises;

a pair of amplification oligonucleotides for amplifying the relevant portion to exon 6 in the cDNA coding eNOS by PCR; and the restriction enzyme FokI.

9. The process of claim 1 in which the detection of the presence of the changes is performed by amplifying a portion encompassing the 815 position in SEQ ID NO:1 in the 5'-flanking region of the eNOS gene by means of PCR, digesting the amplified fragments with the restriction enzyme MspI, and electrophoresing the fragments digested with the enzyme.

10. A diagnostic coronary artery spasm-associated disease kit, which comprises;

a pair of amplification oligonucleotides for amplifying a portion encompassing the 815 position in SEQ ID NO:1 in the 5'-flanking region of the eNOS gene by PCR; and the restriction enzyme MspI.

11. The process of claim 1 in which the detection of the presence of the changes is performed by amplifying a portion encompassing the −1468 position in the 5'-flanking region of the eNOS gene by means of PCR, digesting the amplified fragments with the restriction enzyme MboI, and electrophoresing the fragments digested with the enzyme.

12. A diagnostic coronary artery spasm-associated disease kit, which comprises;

a pair of amplification oligonucleotides for amplifying a portion encompassing the 133 position in SEQ ID NO:1 in the 5'-flanking region of the eNOS gene by PCR; and the restriction enzyme MboI.

13. A method for diagnosing a coronary artery spasm-associated disease, which comprises detecting the presence of any one or more nucleotide change(s) in the eNOS gene as defined in claim 1 which are responsible for the coronary artery spasm-associated disease.

* * * * *

SEQUENCE LISTING

```
<160> NUMBER OF SEQ ID NOS: 72

<210> SEQ ID NO 1
<211> LENGTH: 9208
<212> TYPE: DNA
<213> ORGANISM: Homo sapiens
<220> FEATURE:
<223> OTHER INFORMATION: nnnnnnnnnn = Intervening sequences of introns

<400> SEQUENCE: 1
atctgatgct gcctgtcacc ttgaccctga ggatgccagt cacagctcca ttaactggaa      60
cctaggaaaa tgagtcatcc ttggtcatgc gacatttgca aatggtggct taatatgaa     120 gccagacttg ggttctgttg tctcctcccg catggtagga gatgcctgaa aagtagggc      180 tggatcccat gccctgcctc actgggaagg cgaggtggtg gggtggggtg gggcctcagg     240
cttggggtca tgggacaaag cccaggctga atgccgccct tccatctccc tcctcctgag     300
acaggggcag cagggcacac tagtgtgcag gagcagctta tgaggcccct tcaccctcca     360
tcctccaaaa ctggcagacc ccaccttctt ggtgtgaccc cagagctctg agcacagccc     420
gttccttccg cctgccggcc ccccacccag gcccacccca accttatcct ccactgcttt     480
tcagaggagt ctggccaaca caaatcctct tgtttgtttg tctgtctgtc tgctgctcct     540
agtctctgcc tctcccagtc tctgagcttc cgtttctttc ttaaactttc tctcagtctc     600
tgaggtctcg aaatcacgag gcttcgaccc ctgtggacca gatgcccagc tagtggcctt     660
tctccagccc ctcagatgac acagaactac aaacccagc atgcactctg gcctgaagtg      720
cctggagagt gctggtgtac cccacctgca ttctgggaac tgtagtttcc ctagtccccc     780
atgctcccac cagggcatca agctcttccc tggctggctg accctgcctc agccctagtc     840
tctctgctga ctgcggcccc gggaagcgtg cgtcactgaa tgacagggtg ggggtggagg     900
cactggaagg cagcttcctg ctcttttgtg tcccccactt gagtcatggg ggtgtggggg     960
ttccaggaaa ttggggctgg gaggggaagg gatacccctaa tgtcagactc aaggacaaaa    1020
agtcactaca tccttgctgg gcctctatcc ccaagaaccc aaaaggactc aagggtgggg    1080
atccaggagt tcttgtatgt atggggggag gtgaaggaga gaacctgcat gaccctagag    1140
gtccctgtgg tcactgagag tgtgggctgc catcccctgc tacagaaacg gtgctcacct    1200
tctgcccaac cctccaggga aaggcacaca ggggtgaggc cgacgttccg tctggtgcca    1260
catcacagaa ggacctttat gaccccctgg tggctctacc ctgccactcc ccaatgcccc    1320
agcccccatg ctgcagcccc agggctctgc tggacacctg ggctcccact tatcagcctc    1380
```

-continued

```
agtcctcaca gcggaaccca ggcgtccggc cccccaccct tcaggccagc gggcgtggag   1440
ctgaggcttt agagcctccc agccgggctt gttcctgtcc cattgtgtat gggatagggg   1500
cggggcgagg gccagcactg gagagccccc tcccactgcc ccctcctctc ggtcccctcc   1560
ctcttcctaa ggaaaaggcc agggctctgc tggagcaggc agcagagtgg acgcacagta   1620
acatgggcaa cttgaagagc gtggcccagg agcctgggcc accctgcggc ctggggctgg   1680
ggctgggcct tgggctgtgc ggcaagcagg gcccagccac ccggcccct gagcccagcc   1740 gggccccagc atccctactc ccaccagcgc cagaacacag gtaagggcca ggcagctagg   1800
agcaggtggg caacaagggt ggtgtcaagg cctgaagcct ggggctggga aggtctggaa   1860
cttnnnnnnn nnntggggaa cgccagaagg catgcggcag gtgggctgtg agatcgccag   1920
tgctgtaaca ggggcctccg ggtgacatct gggaaggctg aaaggaaaca aacccttcct   1980
gatgacccta tccctggctc ccaacagccc ccgagctcc ccgctaaccc agcccccaga   2040
ggggcccaag ttccctcgtg tgaagaactg ggaggtgggg agcatcacct atgacaccct   2100
cagcgcccag gcgcagcagg taaggccggc atgcccctgtc cccatcgtct ccagggaaag   2160
ggtgggtaag gcctggcctc agatgggggcc ggagagggaa gctcaaccct tctttgaatt   2220
ggtcccttgt ttccaaaaag aggagaggac tgggnnnnnn nnnntgcacc cctcctccct   2280
gcccccaact cccatcccac ccctgcaccc tggcctgtcc tgacctttgc actccctcga   2340
cccaggatgg gccctgcacc ccaagacgct gcccgggctc cctggtattt ccacggaaac   2400
tacagggccg gccctccccc ggcccccgg cccctgagca gctgctgagt caggcccggg   2460
acttcatcaa ccagtactac agctccatta agaggtgaca gcttcccgga cgccacagcc   2520
tcccttgtcc cactgaggcc ccagaaaccc cgtgacgacc ttcccatgnn nnnnnnnnac   2580
acaacttcct gcttgtcccc ttcccacccc tctcctcccc aggagcggct cccaggccca   2640
cgaacagcgg cttcaagagg tggaagccga ggtggcagcc acaggcacct accagcttag   2700
ggagagcgag ctggtgttcg gggctaagca ggcctggcgc aacgctcccc gctgcgtggg   2760
ccggatccag tgggggaagc tgcaggtgcg gctggccagc gactgagaga cccgggcgct   2820
accaaaaggg gagcggggtg gcggggcagt tcctaaggct tcccggggc tgggaggtcc   2880 caaacnnnnn nnnnncctct ggagctgata ctcaagaccc ccgtctctc tcctcaccct   2940 cctctcccgc tgcctcggct ggctcaggtg ttcgatgccc gggactgcag gtctgcacag   3000
gaaatgttca cctacatctg caaccacatc aagtatgcca ccaaccgggg caaccttcgg   3060
tgagtgcccc ccaccatgcc aggccccagc cttcttcccc aaggcaggga aggcggggct   3120
ctgaccagct ctttccccat gcgtgccagc tcggccatca cagtgttccc gcagcgctgc   3180
cctggccgag gagacttccg aatctggaac agccagctgg tgcgctacgc gggctaccgg   3240
cagcaggacg gctctgtgcg gggggaccca gccaacgtgg agatcaccga ggtgggcacc   3300
gagggccacc catgagggtg tccccaaggt ggagaatgag gaaaccagtg ggagaaggct   3360
cgggnnnnnn nnntggagg ggtccctgag gagggcatga ggctcagccc cagaaccccc   3420
tctggcccac tccccacagc tctgcattca gcacggctgg accccaggaa acggtcgctt   3480
cgacgtgctg cccctgctgc tgcaggcccc agatgagccc ccagaactct tccttctgcc   3540
ccccgagctg gtccttgagg tgcccctgga gcaccccacg tgagcaccaa agggattgac   3600
tgggtgggat ggaggggggcc atccctgagc ctctcaagaa gggcctgcaa ggggggtgctg   3660 atcccacacc ccaacacccc caggctggag tggtttgcag ccctgggcct gcgctggtac   3720
```

-continued

```
gccctcccgg cagtgtccaa catgctgctg gaaattgggg gcctggagtt ccccgcagcc     3780
cccttcagtg gctggtacat gagcactgag atcggcacga ggaacctgtg tgaccctcac     3840
cgctacaaca tcctggaggt gaggtgcggg atggggctcg ggnnnnnnnn nnccttccag     3900
ccatgtacgg gaaacagaga tagtctcccc accccacccc cgtgatcacc tctgtcccta     3960
ccgatgccac acacccttct gccccaggat gtggctgtct gcatggacct ggatacccgg     4020
accacctcgt ccctgtggaa agacaaggca gcagtggaaa tcaacgtggc cgtgctgcac     4080
agttaccagg tgcagaggcc cagactggcc aggaaggcaa agggtttgca tacgggggca     4140 gcagggcnn nnnnnnnngt ggtggaggaa gaatgggcga ggtctgtggg tctggtttga     4200
gcctctcccc ctctctctcc cttccagcta gccaaagtca ccatcgtgga ccaccacgcc     4260
gccacggcct ctttcatgaa gcacctggag aatgagcaga aggccagggg gggctgccct     4320
gcagactggg cctggatcgt gcccccatc tcggcagcc tcactcctgt tttccatcag      4380
gagatggtca actatttcct gtccccggcc ttccgctacc aggtgcccac cctaactggc     4440
tctgcgcctg ggcccagctc taattctaag cagcccctgg ggacctctaa cctttccttt     4500
tctttacctc cctcccaacc catcatctct ctgcaagcca gaccctgga aggggagtgc      4560 cgccaagggc accggcatca ccaggaagaa gacctttaaa gaagtggcca agtgggtccc     4620
ctgggagccc cgctctccca cacacaccct gggggcccca ctctccccca cacccctgg      4680 gggaccctgc cccagcagtg ttctgggcct accactcagt atcccaaaac cctgttgtga     4740
gggggttgga cccttgcctg ggaggccct gcctctgtgc acccaggaca ccctcacacc      4800
ttcctctccc gcagcgccgt gaagatctcc gcctcgctca tgggcacggt gatggcgaag     4860
cgagtgaagg cgacaatcct gtatggctcc gagaccggcc gggcccagag ctacgcacag     4920
cagctgggga gactcttccg gaaggctttt gatccccggg tagggctnnn nnnnnngga     4980 ggccagagtg aggagggcag ggcctccggg ggccacagca cccaggacat ctgtcttccc     5040
acccacaggt cctgtgtatg gatgagtatg acgtggtgtc cctcgaacac gagacgctgg     5100
tgctggtggt aaccagcaca tttgggaatg gggatccccc ggagaatgga gaggtgagaa     5160
cttccaggaa aggggctgct gggaatgagg agagactcnn nnnnnnnntg gtacagtttt     5220
aaacttctat gtagtttgaa atgaaagaaa actaaccctg atgcaaacac tcccctcgcc     5280
agagctttgc agctgccctg atggagatgt ccggccccta caacagctcc cctcggccgg     5340
aacagcacaa gtgagttggg tgagagtttg ggggagnnnn nnnnnnctag cctgtatccc     5400
cagggccctg tgacaacctt gtctttgtcc tctcttgcca ggagttataa gatccgcttc     5460
aacagcatct cctgctcaga cccactggtg tcctcttggc ggcggaagag gaaggagtcc     5520
agtaacacag acagtgcagg ggccctgggc accctcaggt cagggcctca ccaagagggg     5580
tgcaacgggt gggcaagctg cctgggcaaa cgtggcctgc aaagggagct ccactgacga     5640
cccctgcacc ccaggttctg tgtgttcggg ctcggctccc gggcataccc ccacttctgc     5700
gcctttgctc gtgccgtgga cacacggctg gaggaactgg gcggggagcg gctgctgcag     5760
ctgggccagg gcgacgagct gtgcggccag gaggaggcct tccgaggctg ggcccaggct     5820
gccttccagg tgagcccagc ccagcccctg ctctgactcc tgcccctgg gatgcctcct      5880 cctgcctcac tctgccctga ttctgtttgg ttctttggtc ccttnnnnnn nnnnccagga     5940
gcaagacgca gtgaagccgc ccaggcgcct cactagggcg accctggtg gcgggaggtc      6000 ctcagccctc acccgctgtc ccgcaggccg cctgtgagac cttctgtgtg ggagaggatg     6060
ccaaggccgc cgcccgagac atcttcagcc ccaaacggag ctggaagcgc cagaggtacc     6120
```

-continued

```
ggctgagcgc ccaggccgag ggcctgcagt tgctgccagg tgggccctgc ctcaccctaa      6180
cccggctggt tctctgaggc ccccacaccc cgggactaaa gcactctggg gccaggccct      6240
gctccctagc tcaggctgcc tcatttgccc ctccccgccc ccagtctga tccacgtgca       6300 caggcggaag atgttccagg ctacaatccg ctcagtggaa aacctgcaaa gcagcaagtc      6360
cacgtgagga cgacggcttt accgccccca caccctgtc ctgaacaccc tgaccctgga      6420
ccctcctcct cccacattct cccgccccca ccctctctg actccccata agtgccctc       6480 tccccacccc caggagggcc accatcctgg tgcgcctgga caccggaggc caggaggggc     6540
tgcagtacca gccgggggac cacataggtg tctgcccgcc caaccggccc ggccttgtgg     6600
aggcgctgct gagccgcgtg gaggacccgc cggcgcccac tgagcccgtg gcagtagagc     6660
agctggagaa gggcagccct ggtgaggggc agcctgggaa gcaacagggc acccagccc      6720 catgcccagc ccccaccccn nnnnnnnng caggctctct aacagtcacc aaaacacaaa      6780
catcagccca ggtactgcag tcctgctggg ccctgtcctc agagctccct gtgcactatc     6840
cccaggtggc cctccccccg gctgggtgcg ggaccccgg ctgccccgt gcacgctgcg      6900 ccaggctctc accttcttcc tggacatcac ctccccaccc agccctcagc tcttgcggct     6960
gctcagcacc ttggcagaag agcccaggga acagcaggag ctggaggccc tcagccaggt   7020
tgggggccac cccaatgagg cacaggggct agagagacgg gatgagctgg ggggaccccca    7080 gtggcaggaa accccatgn nnnnnnnna accctaaaga ggctcagtgg gggagggggtc      7140 aagaagggag gttactagga agggctatgg ggcctccaac ccactgcatc ctgccccgcc     7200
aggatccccg acgctacgag gagtggaagt ggttccgctg ccccacgctg ctggaggtgc     7260
tggagcagtt cccgtcggtg gcgctgcctg ccccactgct cctcacccag ctgcctctgc    7320
tccagccccg gtactactca gtcagctcgg cacccagcac ccaccaagga gagatccacc    7380
tcactgtagc tgtgctggca tacaggactc agggtgaggc aacaagcagg agcaggcctg    7440
gccacagcag ggttgggacc ggcccctctc tggcccctca ccggcctctc cttcccaccc    7500
ccagatgggc tgggcccccct gcactatgga gtctgctcca cgtggctaag ccagctcaag   7560
cccggagacc ctgtgccctg cttcatccgg gggtaagtga gatggaagac ttggtgggga   7620
gctgcccagg gtcagggtgg cagctttggt gaggagtgtc actggtgagg ggtnnnnnnn   7680
nnnaggggac ctgatggagt gtctctcctg ccagggctcc ctccttccgg ctgccacccg    7740
atcccagctt gccctgcatt ctggtgggtc caggcactgg cattgccccc ttccggggat    7800
tctggcagga gcggctgcat gacattgaga gcaaaggtga ggctgggcac taaaggactg    7860
cctgaaggga gtcacacaat ctagggacag aggggtgggg ctgnnnnnnn nnngggaggc    7920
cccactagca ctgtgccccg gagaagagcc ttcccaaccc ggggttgctt gcagggctgc    7980
agcccactcc catgactttg gtgttcggct gccgatgctc ccaacttgac catctctacc    8040
gcgacgaggt gcagaacgcc cagcagcgcg gggtgtttgg ccgagtcctc accgccttct    8100
cccgggaacc tgacaacccc aagtgtgag acctgaggcg cgcaatggta acctgaagat    8160
agggagagag gggaggactc gcgnnnnnnn nnnccgcgcc cacccccacc agggcccgcc    8220 ctaacccccgc cgccccgcag acctacgtgc aggacatcct gaggacggag ctggctgcgg   8280
aggtgcaccg cgtgctgtgc ctcgagcggg gccacatgtt tgtctgcggc gatgttacca    8340
tggcaaccaa cgtcctgcag accgtgcagc gcatcctggc gacggagggc gacatggagc   8400
tggacgaggc cggcgacgtc atcggcgtgc tgcgggtgcg gagggggcggg ccgggcctga   8460
```

-continued

| | |
|---|---|
| gcgtgcgggg ttcctgctaa ggtctccgag tcgggttctg atccactgtg ctcttttccg | 8520 |
| acaggatcag caacgctacc acgaagacat tttcgggctc acgctgcgca cccaggaggt | 8580 |
| gacaagccgc atacgcaccc agagcttttc cttgcaggag cgtcagttgc ggggcgcagt | 8640 |
| gccctgggcg ttcgaccctc ccggctcaga caccaacagc ccctgagagc cgcctggctt | 8700 |
| tcccttccag ttccgggaga cgggctgccc gactcaggtc cgcccgacca ggatcagccc | 8760 |
| cgctcctccc ctcttgaggt ggtgccttct cacatctgtc cagaggctgc aaggattcag | 8820 |
| cattattcct ccaggaagga gcaaaacgcc tcttttccct ctctaggcct gttgcctcgg | 8880 |
| gcctgggtcc gccttaatct ggaaggcccc tcccagcagc ggtaccccag ggcctactgc | 8940 |
| cacccgcttc ctgtttctta gtcgaatgtt agattcctct tgcctctctc aggagtatct | 9000 |
| tacctgtaaa gtctaatctc taaatcaagt atttattatt gaagatttac cataagggac | 9060 |
| tgtgccagat gttaggagaa ctactaaagt gcctacccca gctcatgtgg attacagttt | 9120 |
| ttttttttg tttttttttt tttgaaacgg agtctccctc tgccgcccgg gctggagtgc | 9180 |
| agtggcgtga tccgttgacc tgcaggtc | 9208 |

<210> SEQ ID NO 2
<211> LENGTH: 3612
<212> TYPE: DNA
<213> ORGANISM: Homo sapiens

<400> SEQUENCE: 2

| | |
|---|---|
| atgggcaact tgaagagcgt ggcccaggag cctgggccac cctgcggcct ggggctgggg | 60 |
| ctgggccttg gctgtgcgg caagcagggc ccagccaccc cggcccctga gcccagccgg | 120 |
| gccccagcat ccctactccc accagcgcca gaacacagcc cccgagctc cccgctaacc | 180 |
| cagcccccag aggggcccaa gttccctcgt gtgaagaact gggaggtggg gagcatcacc | 240 |
| tatgacaccc tcagcgccca ggcgcagcag gatgggccct gcaccccaag acgctgcctg | 300 |
| ggctccctgg tatttccacg gaaactacag ggccggccct ccccggcccc ccggccccct | 360 |
| gagcagctgc tgagtcaggc ccgggacttc atcaaccagt actacagctc cattaagagg | 420 |
| agcggctccc aggcccacga acagcggctt caagaggtgg aagccgaggt ggcagccaca | 480 |
| ggcacctacc agcttaggga gagcgagctg gtgttcgggg ctaagcaggc ctggcgcaac | 540 |
| tgcaggtctg cacaggaaat gttcacctac atctgcaacc acatcaagta tgccaccaac | 660 |
| cggggcaacc ttcgctcggc catcacagtg ttcccgcagc gctgccctgg ccgaggagac | 720 |
| ttccgaatct ggaacagcca gctggtgcgc tacgcgggct accggcagca ggacggctct | 780 |
| gtgcgggggg acccagccaa cgtggagatc accgagctct gcattcagca cggctggacc | 840 |
| ccaggaaacg gtcgcttcga cgtgctgccc ctgctgctgc aggccccaga tgagccccca | 900 |
| gaactcttcc ttctgccccc cgagctggtc cttgaggtgc cctggagca ccccacgctg | 960 |
| gagtggtttg cagccctggg cctgcgctgg tacgccctcc cggcagtgtc caacatgctg | 1020 |
| ctggaaattg gggcctgga gttccccgca gccccttca gtggctggta catgagcact | 1080 |
| gagatcggca cgaggaacct gtgtgaccct caccgctaca acatcctgga ggatgtggct | 1140 |
| gtctgcatga cctggatac ccggaccacc tcgtccctgt ggaaagacaa ggcagcagtg | 1200 |
| gaaatcaacg tggccgtgct gcacagttac cagctagcca agtcaccat cgtggaccac | 1260 |
| cacgccgcca cggcctcttt catgaagcac ctggagaatg agcagaaggc caggggggc | 1320 |
| tgccctgcag actgggcctg gatcgtgccc cccatctcgg gcagcctcac tcctgttttc | 1380 |

-continued

```
catcaggaga tggtcaacta tttcctgtcc ccggccttcc gctaccagcc agaccctgg    1440 aaggggagtg ccgccaaggg caccggcatc accaggaaga agacctttaa agaagtggcc    1500
aacgccgtga agatctccgc ctcgctcatg ggcacggtga tggcgaagcg agtgaaggcg    1560
acaatcctgt atggctccga gaccggccgg gcccagagct acgcacagca gctggggaga    1620
ctcttccgga aggcttttga tccccgggtc ctgtgtatgg atgagtatga cgtggtgtcc    1680
ctcgaacacg agacgctggt gctggtggta accagcacat ttgggaatgg ggatccccg    1740 gagaatggag agagctttgc agctgccctg atggagatgt ccggcccta caacagctcc    1800 cctcggccgg aacagcacaa gagttataag atccgcttca acagcatctc ctgctcagac    1860
ccactggtgt cctcttggcg gcggaagagg aaggagtcca gtaacacaga cagtgcaggg    1920
gccctgggca ccctcaggtt ctgtgtgttc gggctcggct cccgggcata ccccacttc    1980 tgcgcctttg ctcgtgccgt ggacacacg ctggaggaac tgggcgggga gcggctgctg    2040
cagctgggcc agggcgacga gctgtgcggc caggaggagg ccttccgagg ctgggcccag    2100
gctgccttcc aggccgcctg tgagaccttc tgtgtgggag aggatgccaa ggccgccgcc    2160
cgagacatct tcagccccaa acggagctgg aagcgccaga ggtaccggct gagcgcccag    2220
gccgagggcc tgcagttgct gccaggtctg atccacgtgc acaggcggaa gatgttccag    2280
gctacaatcc gctcagtgga aaacctgcaa agcagcaagt ccacgagggc caccatcctg    2340
gtgcgcctgg acaccggagg ccaggagggg ctgcagtacc agccggggga ccacataggt    2400
gtctgcccgc ccaaccggcc cggccttgtg gaggcgctgc tgagccgcgt ggaggacccg    2460
ccggcgccca ctgagcccgt ggcagtagag cagctggaga agggcagccc tggtggccct    2520
ccccccggct gggtgcggga cccccggctg ccccgtgca cgctgcgcca ggctctcacc    2580
ttcttcctgg acatcacctc cccacccagc cctcagctct gcggctgct cagcaccttg    2640 gcagaagagc ccagggaaca gcaggagctg gaggccctca gccaggatcc ccgacgctac    2700
gaggagtgga agtggttccg ctgccccacg ctgctggagg tgctggagca gttcccgtcg    2760
gtggcgctgc ctgccccact gctcctcacc cagctgcctc tgctccagcc ccggtactac    2820
tcagtcagct cggcacccag cacccaccca ggagagatcc acctcactgt agctgtgctg    2880
gcatacagga ctcaggatgg gctggggccc ctgcactatg gagtctgctc cacgtggcta    2940
agccagctca gcccggaga ccctgtgccc tgcttcatcc ggggggctcc ctccttccgg    3000
ctgccacccg atcccagctt gccctgcatc ctggtgggtc caggcactgg cattgccccc    3060
ttccggggat ctggcagga gcggctgcat gacattgaga gcaaagggct gcagcccact    3120
cccatgactt tggtgttcgg ctgccgatgc tcccaacttg accatctcta ccgcgacgag    3180
gtgcagaacg cccagcagcg cggggtgttt ggccgagtcc tcaccgcctt ctcccgggaa    3240
cctgacaacc ccaagaccta cgtgcaggac atcctgagga cggagctggc tgcggaggtg    3300
caccgcgtgc tgtgcctcga gcggggccac atgtttgtct gcggcgatgt taccatggca    3360
accaacgtcc tgcagaccgt gcagcgcatc ctggcgacgg agggcgacat ggagctggac    3420
gaggccggcg acgtcatcgg cgtgctgcgg gatcagcaac gctaccacga agacattttc    3480
gggctcacgc tgcgcaccca ggaggtgaca agccgcatac gcacccagag ctttccttg    3540 caggagcgtc agttgcgggg cgcagtgccc tgggcgttcg accctccgg ctcagacacc    3600 aacagcccct ga                                                       3612
```

```
<210> SEQ ID NO 3
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 3
cagcagagtg gacgcacagt aac                                          23

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 4
ttgttgccca cctgctccta gctg                                         24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 5
aacccttcct gatgaccta tccc                                      24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 6
cttacccacc ctttccctgg agac                                         24

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 7
tcctgacctt tgcactccct cga                                          23

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 8
atgggaaggt cgtcacgggg tttc                                         24

<210> SEQ ID NO 9
<211> LENGTH: 24
<212> TYPE: DNA
```

<213> ORGANISM: Artificial Sequence
<220> FEATURE:
<223> OTHER INFORMATION: Description of Artificial Sequence: Synthetic
      Primers

<400> SEQUENCE: 9
acaacttcct gcttgtcccc ttcc                                          24

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 10
accccgctcc cctttggta                                                20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 11
tctggagctg atactcaaga ccc                                           23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 12
cgcatgggga aagagctggt caga                                          24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 13
tctgaccagc tctttcccca tgcg                                          24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 14
ccactggttt cctcattctc cacc                                          24

<210> SEQ ID NO 15
<211> LENGTH: 22
<212> TYPE: DNA
<213> ORGANISM: Artificial Sequence

```
<220> FEATURE:
<223> OTHER INFORMATION: Description of Artificial Sequence: Synthetic
      Primers

<400> SEQUENCE: 15
aaggcaggag acagtggatg ga                                              22

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 16
cccagtcaat ccctttggtg ctca                                            24

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 17
gctgatccca cacccaaca                                                  20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 18
tgccttggac aggtgcattc                                                 20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 19
tgatcacctc tgtccctacc ga                                              22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 20
atgcaaaccc tttgccttcc tg                                              22

<210> SEQ ID NO 21
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      Primers

<400> SEQUENCE: 21
aagaatgggc gaggtctgtg ggt                                              23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 22 cagggggctgc ttagaattag agc                                             23

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 23
tccctcccaa cccatcatct ctct                                             24

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 24
agtggtaggc ccagaacact gct                                              23

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 25
caggacaccc tcacaccttc ctct                                             24

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 26
tctttctagc tccctgctcc c                                                21

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
```

Primers

<400> SEQUENCE: 27
acagcaccca ggacatctgt cttc                                              24

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 28
agcccctttc ctggaagttc tca                                               23

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 29
tgatgtcaaa cactcccctc g                                                 21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 30
aaaacggact tgaggcacag                                                   20

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 31
gtgacaacct tgtctttgtc c                                                 21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 32
tcgtcagtgg agctcccttt                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

```
<400> SEQUENCE: 33
aaagggagct ccactgacga                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 34
agaatcaggg cagagtgagg                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 35
agcaagacgc agtgaagccg                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 36
tggccccaga gtgctttagt                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 37
actaaagcac tctggggcca                                              20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 38
agggtcaggg tgttcaggac a                                            21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      Primers
```

```
<400> SEQUENCE: 39
tgtcctgaac accctgaccc t                                              21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 40
gctggtgtgc cctgttgctt                                                20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 41
ctccctgtgc actatcccca                                                20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 42
tctagcccct gtgcctcatt                                                20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 43
tccaacccac tgcatcctgc                                                20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 44
tgctcctgct tgttgcctca                                                20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 45
```
tgaggcaaca agcaggagca                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 46
caccaagtct tccatctcac                                                    20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 47
atggagtgtc tctcctgcca                                                    20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 48
ttcaggcagt cctttagtgc                                                    20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 49
agaagagcct tcccaacccg                                                    20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 50
atcttcaggt taccattgcg                                                    20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 51
cagacctacg tgcaggacat                                              20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 52
accttagcag gaaccccgca                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 53
gttctgatcc actgtgctct                                              20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 54
tctcccggaa ctggaaggga                                              20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 55
acaccaacag cccctgagag                                              20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 56
tggcagtagg ccctggggta                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 57
ttaatctgga aggcccctcc                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 58
gagggagact ccgtttcaaa                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 59
atgctcccac cagggcatca                                              20

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 60
gtccttgagt ctgacattag gg                                           22

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 61
tcagtctctg aggtctcgaa                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 62
tgatgccctg gtgggagcat                                              20

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 63
ccattaactg gaacctagga a                                            21

```
<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 64
agcctgggct ttgtcccatg a                                              21

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 65
tctgaccagc tctttcccca ttcg                                           24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 66
ccactggttt cctcattctc cacc                                           24

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 67
ctccagcccc tcagatga                                                  18

<210> SEQ ID NO 68
<211> LENGTH: 17
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 68
tccagcccct cagatgg                                                   17

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 69
gtccttgagt ctgacattag gg                                             22
```

-continued

```
<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 70
aatgagtcat ccttggtcat g                                              21

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 71
gggtttgtag ttctgtgt                                                  18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 72
gggtttgtag ttctgtgc                                                  18
```